US009615748B2

(12) United States Patent
Tearney et al.

(10) Patent No.: US 9,615,748 B2
(45) Date of Patent: Apr. 11, 2017

(54) ENDOSCOPIC BIOPSY APPARATUS, SYSTEM AND METHOD

(75) Inventors: Guillermo J. Tearney, Cambridge, MA (US); Brett E. Bouma, Quincy, MA (US); Dongkyun Kang, Somerville, MA (US); Melissa J. Suter, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 16 days.

(21) Appl. No.: 12/690,686

(22) Filed: Jan. 20, 2010

(65) Prior Publication Data

US 2010/0210937 A1    Aug. 19, 2010

Related U.S. Application Data

(60) Provisional application No. 61/145,914, filed on Jan. 20, 2009, provisional application No. 61/184,180, filed on Jun. 4, 2009.

(51) Int. Cl.
*A61B 6/00* (2006.01)
*A61B 5/00* (2006.01)
*A61B 5/02* (2006.01)

(52) U.S. Cl.
CPC .......... *A61B 5/0066* (2013.01); *A61B 5/0068* (2013.01); *A61B 5/0086* (2013.01); *A61B 5/0075* (2013.01)

(58) Field of Classification Search
CPC ... A61B 5/0084; A61B 5/0066; A61B 5/0075; A61B 5/0068; A61B 2018/00982;
(Continued)

(56) References Cited

U.S. PATENT DOCUMENTS 3,090,753 A    5/1963   Matuszak et al.
3,872,407 A    3/1975   Hughes
(Continued)

FOREIGN PATENT DOCUMENTS

CN    1550203      12/2004
DE    10351319     6/2005
(Continued)

OTHER PUBLICATIONS

R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
(Continued)

*Primary Examiner* — Elmer Chao
(74) *Attorney, Agent, or Firm* — Andrews Kurth Kenyon LLP

(57) ABSTRACT

Exemplary embodiments of apparatus, method and system for determining a position on or in a biological tissue can be provided. For example, using such exemplary embodiment, it is possible to control the focus of an optical imaging probe. In another exemplary embodiment, it is possible to implement a marking apparatus together with or into an optical imaging probe. According to one exemplary embodiment, it is possible (using one or more arrangements) to receive information associated with at least one image of at least one portion of the biological tissue obtained using an optical imaging technique. Further, it is possible to, based on the information, cause a visible change on or in at least location of the portion(s) using at least one electro-magnetic radiation.

16 Claims, 13 Drawing Sheets

(58) Field of Classification Search
CPC .. A61B 2018/00577; A61B 2019/5231; A61B 2019/507; A61B 3/102; A61B 18/20; A01B 9/02091; G02B 21/0028
USPC ......... 600/476–480, 407; 128/664, 665, 634, 128/633; 606/2–19
See application file for complete search history.

(56) References Cited

U.S. PATENT DOCUMENTS

| | | |
|---|---|---|
| 4,030,831 A | 6/1977 | Gowrinathan |
| 4,140,364 A | 2/1979 | Yamashita et al. |
| 4,224,929 A | 9/1980 | Furihata |
| 4,479,499 A | 10/1984 | Alfano et al. |
| 4,585,349 A | 4/1986 | Gross et al. |
| 4,601,036 A | 7/1986 | Faxvog et al. |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,827,907 A | 5/1989 | Tashiro et al. |
| 4,834,111 A | 5/1989 | Khanna et al. |
| 4,890,901 A | 1/1990 | Cross, Jr. |
| 4,905,169 A | 2/1990 | Buican et al. |
| 4,909,631 A | 3/1990 | Tan et al. |
| 4,940,328 A | 7/1990 | Hartman |
| 4,966,589 A | 10/1990 | Kaufman |
| 4,984,888 A | 1/1991 | Tobias et al. |
| 4,998,972 A | 3/1991 | Chin et al. |
| 5,085,496 A | 2/1992 | Yoshida et al. |
| 5,121,983 A | 6/1992 | Lee |
| 5,177,488 A | 1/1993 | Wang et al. |
| 5,197,470 A * | 3/1993 | Helfer et al. ................. 600/342 |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,241,364 A | 8/1993 | Kimura et al. |
| 5,250,186 A | 10/1993 | Dollinger et al. |
| 5,251,009 A | 10/1993 | Bruno |
| 5,275,594 A | 1/1994 | Baker |
| 5,281,811 A | 1/1994 | Lewis |
| 5,283,795 A | 2/1994 | Fink |
| 5,302,025 A | 4/1994 | Kleinerman |
| 5,304,173 A | 4/1994 | Kittrell et al. |
| 5,317,389 A | 5/1994 | Hochberg et al. |
| 5,318,024 A | 6/1994 | Kittrell et al. |
| 5,333,144 A | 7/1994 | Liedenbaum et al. |
| 5,348,003 A | 9/1994 | Caro |
| 5,394,235 A | 2/1995 | Takeuchi et al. |
| 5,400,771 A | 3/1995 | Pirak et al. |
| 5,404,415 A | 4/1995 | Mori et al. |
| 5,414,509 A | 5/1995 | Veligdan |
| 5,424,827 A | 6/1995 | Horwitz et al. |
| 5,479,928 A | 1/1996 | Cathignoal et al. |
| 5,522,004 A | 5/1996 | Djupsjobacka et al. |
| 5,555,087 A | 9/1996 | Miyagawa et al. |
| 5,565,983 A | 10/1996 | Barnard et al. |
| 5,565,986 A | 10/1996 | Knuttel |
| 5,566,267 A | 10/1996 | Neuberger |
| 5,628,313 A | 5/1997 | Webster, Jr. |
| 5,635,830 A | 6/1997 | Itoh |
| 5,649,924 A | 7/1997 | Everett et al. |
| 5,701,155 A | 12/1997 | Wood et al. |
| 5,730,731 A | 3/1998 | Mollenauer et al. |
| 5,748,318 A | 5/1998 | Maris et al. |
| 5,752,518 A | 5/1998 | McGee et al. |
| 5,785,651 A | 7/1998 | Baker et al. |
| 5,801,831 A | 9/1998 | Sargoytchev et al. |
| 5,810,719 A | 9/1998 | Toida |
| 5,817,144 A | 10/1998 | Gregory et al. |
| 5,829,439 A | 11/1998 | Yokosawa et al. |
| 5,836,877 A | 11/1998 | Zavislan et al. |
| 5,840,031 A | 11/1998 | Crowley |
| 5,910,839 A | 6/1999 | Erskine et al. |
| 5,912,764 A | 6/1999 | Togino |
| 5,926,592 A | 7/1999 | Harris et al. |
| 5,955,737 A | 9/1999 | Hallidy et al. |
| 5,975,697 A | 11/1999 | Podoleanu et al. |
| 5,994,690 A | 11/1999 | Kulkarni et al. |
| 5,995,223 A | 11/1999 | Power |
| 6,007,996 A | 12/1999 | McNamara et al. |
| 6,010,449 A | 1/2000 | Selmon et al. |
| 6,016,197 A | 1/2000 | Krivoshlykov |
| 6,020,963 A | 2/2000 | Dimarzio et al. |
| 6,025,956 A | 2/2000 | Nagano et al. |
| 6,037,579 A | 3/2000 | Chan et al. |
| 6,045,511 A | 4/2000 | Ott et al. |
| 6,052,186 A | 4/2000 | Tsai |
| 6,078,047 A | 6/2000 | Mittleman et al. |
| 6,094,274 A | 7/2000 | Yokoi |
| 6,107,048 A | 8/2000 | Goldenring et al. |
| 6,111,645 A | 8/2000 | Tearney et al. |
| 6,245,026 B1 | 6/2001 | Campbell et al. |
| 6,249,381 B1 | 6/2001 | Suganuma |
| 6,249,630 B1 | 6/2001 | Stock et al. |
| 6,272,268 B1 | 8/2001 | Miller et al. |
| 6,297,018 B1 | 10/2001 | French et al. |
| 6,301,048 B1 | 10/2001 | Cao et al. |
| 6,341,036 B1 | 1/2002 | Tearney et al. |
| 6,374,128 B1 | 4/2002 | Toida et al. |
| 6,377,349 B1 | 4/2002 | Fercher |
| 6,396,941 B1 | 5/2002 | Bacus et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,501,551 B1 | 12/2002 | Tearney et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,560,259 B1 | 5/2003 | Hwang et al. |
| 6,567,585 B2 | 5/2003 | Harris |
| 6,593,101 B2 | 7/2003 | Richards-Kortum et al. |
| 6,611,833 B1 | 8/2003 | Johnson et al. |
| 6,654,127 B2 | 11/2003 | Everett et al. |
| 6,657,730 B2 | 12/2003 | Pfau et al. |
| 6,658,278 B2 | 12/2003 | Gruhl |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,884 B1 | 5/2004 | Freeman et al. |
| 6,757,467 B1 | 6/2004 | Rogers |
| 6,790,175 B1 | 9/2004 | Furusawa et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,996,549 B2 | 2/2006 | Zhang et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |

(56) References Cited

U.S. PATENT DOCUMENTS

| | | |
|---|---|---|
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,911,621 B2 | 3/2011 | Motaghiannezam et al. |
| 7,969,578 B2 | 6/2011 | Yun et al. |
| 7,973,936 B2 | 7/2011 | Dantus |
| 8,315,282 B2 | 11/2012 | Huber et al. |
| 2001/0020126 A1 | 9/2001 | Swanson et al. |
| 2001/0036002 A1 | 11/2001 | Tearney et al. |
| 2001/0055462 A1 | 12/2001 | Seibel |
| 2002/0024015 A1 | 2/2002 | Hoffmann et al. |
| 2002/0037252 A1 | 3/2002 | Toida et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0068853 A1* | 6/2002 | Adler ............................ 600/160 |
| 2002/0086347 A1 | 7/2002 | Johnson et al. |
| 2002/0091322 A1 | 7/2002 | Chaiken et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0140942 A1 | 10/2002 | Fee et al. |
| 2002/0158211 A1 | 10/2002 | Gillispie |
| 2002/0166946 A1 | 11/2002 | Iizuka et al. |
| 2002/0168158 A1 | 11/2002 | Furusawa et al. |
| 2002/0183623 A1 | 12/2002 | Tang et al. |
| 2003/0001071 A1 | 1/2003 | Mandella et al. |
| 2003/0013973 A1 | 1/2003 | Georgakoudi et al. |
| 2003/0025917 A1 | 2/2003 | Suhami |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0103212 A1 | 6/2003 | Westphal et al. |
| 2003/0108911 A1 | 6/2003 | Klimant et al. |
| 2003/0120137 A1 | 6/2003 | Pawluczyk et al. |
| 2003/0137669 A1 | 7/2003 | Rollins et al. |
| 2003/0165263 A1 | 9/2003 | Hamer et al. |
| 2003/0174339 A1 | 9/2003 | Feldchtein et al. |
| 2003/0191392 A1 | 10/2003 | Haldeman |
| 2003/0220749 A1 | 11/2003 | Chen et al. |
| 2003/0236443 A1* | 12/2003 | Cespedes et al. .............. 600/29 |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0188148 A1 | 9/2004 | Chen et al. |
| 2004/0189999 A1 | 9/2004 | De Groot et al. |
| 2004/0204651 A1 | 10/2004 | Freeman et al. |
| 2004/0239938 A1 | 12/2004 | Izatt |
| 2004/0246490 A1 | 12/2004 | Wang |
| 2004/0246583 A1 | 12/2004 | Mueller et al. |
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0049488 A1 | 3/2005 | Homan |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Wallace et al. |
| 2005/0221270 A1 | 10/2005 | Connelly et al. |
| 2005/0251116 A1* | 11/2005 | Steinke et al. .................... 606/8 |
| 2005/0254059 A1 | 11/2005 | Alphonse |
| 2005/0254061 A1 | 11/2005 | Alphonse et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0081236 A1* | 4/2007 | Tearney et al. .............. 359/390 |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0179487 A1 | 8/2007 | Tearney et al. |
| 2007/0188855 A1 | 8/2007 | Shishkov et al. |
| 2007/0203404 A1 | 8/2007 | Zysk et al. |

(56) References Cited

U.S. PATENT DOCUMENTS

| | | | |
|---|---|---|---|
| 2007/0208400 A1* | 9/2007 | Nadkarni et al. | 607/100 |
| 2007/0223006 A1 | 9/2007 | Tearney et al. | |
| 2007/0233056 A1 | 10/2007 | Yun | |
| 2007/0236700 A1 | 10/2007 | Yun et al. | |
| 2007/0253901 A1 | 11/2007 | Deng et al. | |
| 2007/0258094 A1 | 11/2007 | Izatt et al. | |
| 2007/0263226 A1 | 11/2007 | Kurtz et al. | |
| 2007/0291277 A1 | 12/2007 | Everett et al. | |
| 2008/0002197 A1 | 1/2008 | Sun et al. | |
| 2008/0007734 A1 | 1/2008 | Park et al. | |
| 2008/0013960 A1 | 1/2008 | Tearney et al. | |
| 2008/0021275 A1* | 1/2008 | Tearney et al. | 600/115 |
| 2008/0027429 A1* | 1/2008 | Oyatsu | 606/45 |
| 2008/0049220 A1 | 2/2008 | Izzia et al. | |
| 2008/0070323 A1 | 3/2008 | Hess et al. | |
| 2008/0094613 A1 | 4/2008 | de Boer et al. | |
| 2008/0094637 A1 | 4/2008 | de Boer et al. | |
| 2008/0097225 A1 | 4/2008 | Tearney et al. | |
| 2008/0097709 A1 | 4/2008 | de Boer et al. | |
| 2008/0100837 A1 | 5/2008 | de Boer et al. | |
| 2008/0139906 A1 | 6/2008 | Bussek et al. | |
| 2008/0152353 A1 | 6/2008 | de Boer et al. | |
| 2008/0154090 A1 | 6/2008 | Hashimshony | |
| 2008/0201081 A1 | 8/2008 | Reid | |
| 2008/0204762 A1 | 8/2008 | Izatt et al. | |
| 2008/0218696 A1 | 9/2008 | Mir | |
| 2008/0226029 A1 | 9/2008 | Weir et al. | |
| 2008/0228086 A1 | 9/2008 | Ilegbusi | |
| 2008/0234560 A1 | 9/2008 | Nomoto et al. | |
| 2008/0252901 A1 | 10/2008 | Shimizu | |
| 2008/0265130 A1 | 10/2008 | Colomb et al. | |
| 2008/0297806 A1 | 12/2008 | Motachiannezam | |
| 2008/0308730 A1 | 12/2008 | Vizi et al. | |
| 2009/0004453 A1 | 1/2009 | Murai et al. | |
| 2009/0005691 A1 | 1/2009 | Huang | |
| 2009/0011948 A1 | 1/2009 | Uniu et al. | |
| 2009/0012368 A1 | 1/2009 | Banik et al. | |
| 2009/0012369 A1* | 1/2009 | Robinson et al. | 600/182 |
| 2009/0044799 A1 | 2/2009 | Qiu | |
| 2009/0051923 A1 | 2/2009 | Zuluaga | |
| 2009/0131801 A1 | 5/2009 | Suter et al. | |
| 2009/0192358 A1 | 7/2009 | Jaffer et al. | |
| 2009/0196477 A1 | 8/2009 | Cense et al. | |
| 2009/0209834 A1 | 8/2009 | Fine | |
| 2009/0273777 A1 | 11/2009 | Yun et al. | |
| 2009/0290156 A1 | 11/2009 | Popescu et al. | |
| 2009/0305309 A1 | 12/2009 | Chien et al. | |
| 2009/0306520 A1 | 12/2009 | Schmitt et al. | |
| 2009/0323056 A1 | 12/2009 | Yun et al. | |
| 2010/0086251 A1 | 4/2010 | Xu et al. | |
| 2010/0094576 A1 | 4/2010 | de Boer et al. | |
| 2010/0145145 A1 | 6/2010 | Shi et al. | |
| 2010/0150467 A1 | 6/2010 | Zhao et al. | |
| 2010/0261995 A1 | 10/2010 | Mckenna et al. | |
| 2011/0028967 A1 | 2/2011 | Rollins et al. | |
| 2011/0160681 A1 | 6/2011 | Dacey, Jr. et al. | |
| 2011/0218403 A1 | 9/2011 | Tearney et al. | |

FOREIGN PATENT DOCUMENTS

| | | |
|---|---|---|
| DE | 102005034443 | 2/2007 |
| EP | 0617286 | 2/1994 |
| EP | 0697611 | 2/1996 |
| EP | 0728440 | 8/1996 |
| EP | 1324051 | 7/2003 |
| EP | 2149776 | 2/2010 |
| FR | 2738343 | 8/1995 |
| GB | 2298054 | 8/1996 |
| JP | 6073405 | 4/1985 |
| JP | 361040633 | 3/1986 |
| JP | 62-188001 | 6/1989 |
| JP | 04-056907 | 2/1992 |
| JP | 20040056907 | 2/1992 |
| JP | 5509417 | 11/1993 |
| JP | H8-136345 | 5/1996 |
| JP | H08-160129 | 6/1996 |
| JP | 9-10213 | 1/1997 |
| JP | 9-230248 | 9/1997 |
| JP | 10-213485 | 8/1998 |
| JP | 10-267631 | 10/1998 |
| JP | 10-267830 | 10/1998 |
| JP | 2259617 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000-126116 | 5/2000 |
| JP | 2000-131222 | 5/2000 |
| JP | 2001-4447 | 1/2001 |
| JP | 2001-500026 | 1/2001 |
| JP | 2001-104315 | 4/2001 |
| JP | 2001-174404 | 6/2001 |
| JP | 2001-174744 | 6/2001 |
| JP | 2001-507251 | 6/2001 |
| JP | 2001-508340 | 6/2001 |
| JP | 2007-539336 | 6/2001 |
| JP | 2001-212086 | 7/2001 |
| JP | 2001-212086 | 8/2001 |
| JP | 2008-533712 | 8/2001 |
| JP | 2001-264246 | 9/2001 |
| JP | 2001-515382 | 9/2001 |
| JP | 2001-525580 | 12/2001 |
| JP | 2002-503134 | 1/2002 |
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214127 | 7/2002 |
| JP | 2002-214128 | 7/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-089552 | 3/2004 |
| JP | 2004-113780 | 4/2004 |
| JP | 2004-514920 | 5/2004 |
| JP | 2004-258144 | 9/2004 |
| JP | 2004-317437 | 11/2004 |
| JP | 2005-062850 | 3/2005 |
| JP | 2005-110208 | 4/2005 |
| JP | 2005-510323 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-015134 A | 1/2006 |
| JP | 2006-015134 A | 1/2006 |
| JP | 2006-237359 | 9/2006 |
| JP | 2007-500059 | 1/2007 |
| JP | 2007-075403 | 3/2007 |
| JP | 2007-83053 | 4/2007 |
| JP | 2007-524455 | 8/2007 |
| JP | 2007271761 | 10/2007 |
| JP | 2003-102672 | 4/2012 |
| RU | 2149464 | 5/2000 |
| RU | 2209094 | 7/2003 |
| RU | 2213421 | 9/2003 |
| RU | 2242710 | 12/2004 |
| RU | 2255426 | 6/2005 |
| RU | 2108122 | 6/2006 |
| WO | 79008941 | 10/1979 |
| WO | 9201966 | 2/1992 |
| WO | 9216865 | 10/1992 |
| WO | 9216865 | 10/1993 |
| WO | 96-02184 | 2/1996 |
| WO | 96-04839 | 2/1996 |

(56) References Cited

FOREIGN PATENT DOCUMENTS

| WO | 9800057 | 1/1998 |
|---|---|---|
| WO | 98-35203 | 8/1998 |
| WO | 9848846 | 11/1998 |
| WO | 9944089 | 2/1999 |
| WO | 99-28856 | 6/1999 |
| WO | 99-45838 | 9/1999 |
| WO | 99-45338 | 10/1999 |
| WO | 00-42906 | 7/2000 |
| WO | 00-43730 | 7/2000 |
| WO | 01-04828 | 1/2001 |
| WO | 0101111 | 1/2001 |
| WO | 0127679 | 4/2001 |
| WO | 01-33215 | 5/2001 |
| WO | 01-38820 | 5/2001 |
| WO | 01-42735 | 6/2001 |
| WO | 01-82786 | 11/2001 |
| WO | 02-37075 | 5/2002 |
| WO | 0237075 | 5/2002 |
| WO | 02-45572 | 6/2002 |
| WO | 02-68853 | 6/2002 |
| WO | 02-054027 | 7/2002 |
| WO | 02053050 | 7/2002 |
| WO | 02-083003 | 10/2002 |
| WO | 02084263 | 10/2002 |
| WO | 03-003903 | 1/2003 |
| WO | 03-012405 | 2/2003 |
| WO | 03-013624 | 2/2003 |
| WO | 03013624 | 2/2003 |
| WO | 03046495 | 6/2003 |
| WO | 03046636 | 6/2003 |
| WO | 03053226 | 7/2003 |
| WO | 03062802 | 7/2003 |
| WO | 03-088826 | 10/2003 |
| WO | 03105678 | 12/2003 |
| WO | 2004-037068 | 5/2004 |
| WO | 2004-043251 | 5/2004 |
| WO | 2004057266 | 7/2004 |
| WO | 2004-073501 | 9/2004 |
| WO | 2004-100789 | 11/2004 |
| WO | 2004-105598 | 12/2004 |
| WO | 2005-045362 | 5/2005 |
| WO | 2005-047813 | 5/2005 |
| WO | 2005047813 | 5/2005 |
| WO | 2005082225 | 9/2005 |
| WO | 2006004743 | 1/2006 |
| WO | 2006-020605 | 2/2006 |
| WO | 2006-058187 | 2/2006 |
| WO | 2006038876 | 4/2006 |
| WO | 2006039091 | 4/2006 |
| WO | 2006-050320 | 5/2006 |
| WO | 2006-058187 | 6/2006 |
| WO | 2006059109 | 6/2006 |
| WO | 2006124860 | 11/2006 |
| WO | 2006-131859 | 12/2006 |
| WO | 2007-030835 | 3/2007 |
| WO | 2007028531 | 3/2007 |
| WO | WO 2007/041376 | 4/2007 |
| WO | WO 2007/041376 A1 | 4/2007 |
| WO | 2007083138 | 7/2007 |
| WO | 2007084995 | 7/2007 |
| WO | 2009-033064 | 3/2009 |
| WO | 2011-055376 | 5/2011 |
| WO | 2011-080713 | 7/2011 |

OTHER PUBLICATIONS

R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.

W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.

J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.

D.J. Bowery et al., (1999) "Patterns of Gastritis in Patients with Gastro-Oesophageal Reflux Disease,", Gut, vol. 45, pp. 798-803.

O'Reich et al., (2000) "Expression of Oestrogen and Progesterone Receptors in Low-Grade Endometrial Stromal Sarcomas,", British Journal of Cancer, vol. 82, No. 5, pp. 1030-1034.

M.I. Canto et al., (1999) "Vital Staining and Barrett's Esophagus," Gastrointestinal Endoscopy, vol. 49, No. 3, Part 2, pp. S12-S16.

S. Jackle et al., (2000) "In Vivo Endoscopic Optical Coherence Tomography of the Human Gastrointestinal Tract—Toward Optical Biopsy," Encoscopy, vol. 32, No. 10, pp. 743-749.

E. Montgomery et al., "Reproducibility of the Diagnosis of Dysplasia in Barrett Esophagus: A Reaffirmation," Apr. 2001, Human Pathology, vol. 32, No. 4, pp. 368-378.

H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.

P. Pfau et al., (2003) "Criteria for the Diagnosis of Dysphasia by Endoscopic Optical Coherence Tomography," Gastrointestinal Endoscopy, vol. 58, No. 2, pp. 196-2002.

R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.

X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.

Seltzer et al., (1991) "160 nm Continuous Tuning of a MQW Laser in an External Cavity Across the Entire 1.3 μm Communications Window," Electronics Letters, vol. 27, pp. 95-96.

Office Action dated Jan. 25, 2010 for U.S. Appl. No. 11/537,048.

International Search Report dated Jan. 27, 2010 for PCT/US2009/050553.

International Search Report dated Jan. 27, 2010 for PCT/US2009/047988.

International Search Report dated Feb. 23, 2010 for U.S. Appl. No. 11/445,131.

Office Action dated Mar. 18, 2010 of U.S. Appl. No. 11/844,454.

Office Action dated Apr. 8, 2010 of U.S. Appl. No. 11/414,564.

Japanese Office Action dated Apr. 13, 2010 for Japanese Patent application No. 2007-515029.

International Search Report dated May 27, 2010 for PCT/US2009/063420.

Office Action dated May 28, 2010 for U.S. Appl. No. 12/015,642.

Office Action dated Jun. 2, 2010 for U.S. Appl. No. 12/112,205.

Liptak David C. et al., (2007) "On the Development of a Confocal Rayleigh-Brillouin Microscope" *American Institute of Physics* vol. 78, 016106.

Office Action mailed Oct. 1, 2008 for U.S. Appl. No. 11/955,986.

Invitation of Pay Additional Fees mailed Aug. 7, 2008 for International Application No. PCT/US2008/062354.

Invitation of Pay Additional Fees mailed Jul. 20, 2008 for International Application No. PCT/US2007/081982.

International Search Report and Written Opinion mailed Mar. 7, 2006 for PCT/US2005/035711.

International Search Report and Written Opinion mailed Jul. 18, 2008 for PCT/US2008/057533.

Aizu, Y et al. (1991) "Bio-Speckle Phenomena and Their Application to the Evaluation of Blood Flow" Optics and Laser Technology, vol. 23, No. 4, Aug. 1, 1991.

Richards G.J. et al. (1997) "Laser Speckle Contrast Analysis (LASCA): A Technique for Measuring Capillary Blood Flow Using the First Order Statistics of Laser Speckle Patterns" Apr. 2, 1997.

Gonick, Maria M., et al (2002) "Visualization of Blood Microcirculation Parameters in Human Tissues by Time Integrated Dynamic Speckles Analysis" vol. 972, No. 1, Oct. 1, 2002.

International Search Report and Written Opinion mailed Jul. 4, 2008 for PCT/US2008/051432.

(56) References Cited

OTHER PUBLICATIONS

Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" Optics Letters, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the $19^{th}$ Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.

International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral- and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.

(56) References Cited

OTHER PUBLICATIONS

Summons to attend Oral Proceedings dated Oct. 9, 2009 for European patent application No. 06813365.1.
Office Action dated Dec. 15, 2009 for U.S. Appl. No. 11/549,397.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al, "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report mailed Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).

M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesoscopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
European Search Report daled Jun. 25, 2012 for EP 10733985.5.
Wieser, Wolfgang et al., "Multi-Megahertz OCT: High Quality 3D Imaging at 20 million A-Scans and 4.5 Gvoxels per Second" Jul. 5, 2010, vol. 18, No. 14, Optics Express.
International Search Report and Written Opinion mailed Aug. 30, 2012 for PCT/US2012/035234.
Japanese Notice of Reasons for Rejection dated Oct. 2, 2012 for 2007-543626.
Yoden, K. et al. "An Approach to Optical Reflection Tomograpyhy Along the Geometrial Thickness," Optical Review, vol. 7, No. 5, Oct. 1, 2000.
The First Office Action for Japanese Patent Application No. 2013-263754 dated Sep. 30, 2014.
The Office Action for Japanese Patent Application 2013-263754 dated on Jun. 2, 2015.
The Office Action for Japanese Patent Application No. 2011-546443 dated Feb. 3, 2015.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP 2008-533712.
International Search Report and Written Opinion mailed Feb. 9, 2012 based on PCT/US2011/034810.
Japanese Notice of Reasons for Rejection dated Mar. 27, 2012 for JP 2003-102672.
Japanese Notice of Reasons for Rejection dated May 8, 2012 for JP 2008-533727.

(56) References Cited

OTHER PUBLICATIONS

Korean Office Action dated May 25, 2012 for KR 10-2007-7008116.
Japanese Notice of Reasons for Rejection dated May 21, 2012 for JP 2008-551523.
Japanese Notice of Reasons for Rejection dated Jun. 20, 2012 for JP 2009-546534.
European Official Communication dated Aug. 1, 2012 for EP 10193526.0.
European Search Report dated Jun. 23, 2012 for EP 10733985.5.
Wieser, Wolfgang et al., "Multi-Metahertz OCT: High Quality 3D Imaging at 20 million A-Scans and 4.5 Gvoxels per Second" Jul. 5, 2010, vol. 18, No. 14, Optics Express.
European Communication Pursuant to EPC Article 94(3) for EP 07845206.7 dated Aug. 30, 2012.
International Search Report and Written Opinion mailed Aug. 30, '2012 for PCT/US2012/035234.
Giuliano, Scarcelli et al., "Three-Dimensional Brillouin Confocal Microscopy". Optical Society of American, 2007, CtuV5.
Giuliano, Scarcelli et al., "Confocal Brillouin Microscopy for Three-Dimensional Mechanical Imaging." Nat Photonis, Dec. 9, 2007.
Japanese Notice of Reasons for Rejections dated Oct. 10, 2012 for 2008-553511.
W.Y. Oh et al: "High:Speed Polarization Sensitive Optical Frequency Domain Imaging with Frequency Multiplexing", Optics Express, vol. 16, No. 2, Jan. 1, 2008.
Athey, B.D. et al., "Development and Demonstration of a Networked Telepathology 3-D Imaging, Databasing, and Communication System", 1998 ("C2"), pp. 5-17.
D'Amico, A.V., et al., "Optical Coherence Tomography as a Method for Indentifying Benign and Maliganat Microscopic Structures in the Prostrate Gland", Urology, vol. 55, Isue 5, May 2000 ("C3"), pp. 783-787.
Tearney, G.J. et al., "In Vivo Endoscopic Optical Biopsy with Optical Coherence Tomography", Science, vol. 276, No. 5321, Junl. 27, 1997 ("C6"), pp. 2037-2039.
Japanese Notice of Reasons for Rejections dated Oct. 2, 2012 for 2007-543626.
Canadian Office Action dated Oct. 10, 2012 for 2,514,189.
Japanese Notice of Reasons for Rejections dated Nov. 9, 2012 for JP 2007-530134.
Japanese Notice of Reasons for Rejections dated Nov. 27, 2012 for JP 2009-554772.
Japanese Notice of Reasons for Rejections dated Oct. 11, 2012 for JP 2008-533712.
Yoden, K. et al. "An Approach to Optical Reflection Tomography Along the Geometrial Thickness," Optical Review, vol. 7, No. 5, Oct. 1, 2000.
International Search Report and Written Opinion mailed Oct. 25, 2012 for PCT/US2012/047415.
Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.
European Official Communication dated Feb. 6, 2013 for 04822169.1.
International Search Report mailed Jan. 31, 2013 for PCT/US2012/061135.
Viliyam K. Pratt. Lazernye Sistemy Svyazi. Moskva, Izdatelstvo "Svyaz", 1972. p. 68-70.
International Search Report and Written Opinion mailed Jan. 31, 2013 for PCT/US2012/060843.
European Search Report mailed on Mar. 11, 2013 doe EP 10739129.4.
Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.

M. Kourogi et al: "Programmable High Speed (1MHz) Vernier-mode-locked Frequency-Swept Laser for OCT Imaging", Proceedings of SPIE, vol. 6847, Feb. 7, 2008.
Notice of Reasons for Rejection dated Feb. 5, 2013 for JP 2008-509233.
Notice of Reasons for Rejection dated Feb. 19, 2013 for JP 2008-507983.
European Extended Search Report mailed Mar. 26, 2013 for EP 09825421.1.
Masahiro, Yamanari et al: "polarization-Sensitive Swept-Source Optical Coherence Tomography with Continuous Source Polarization Modulation", Optics Express, vol. 16, No. 8, Apr. 14, 2008.
European Extended Search Report mailed on Feb. 1, 2013 for EP 12171521.3.
Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.
Lee, Seok-Jeong et al., "Ultrahigh Scanning Speed Optical Coherence Tomography Using Optical Frequency Comb Generators", The Japan Soceity of Applied Physics, vol. 40 (2001).
Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.
Notice of Reasons for Rejection mailed on Apr. 16, 2013 for JP 2009-510092.
Bachmann A.H. et al: "Heterodyne Fourier Domain Optical Coherence Tomography for Full Range Probing with High Axial Resolution", Optics Express, OSA, vol. 14, No. 4, Feb. 20, 2006.
European Search Report for 12194876.4 dated Feb. 1, 2013.
International Search Report and Written Opinion for PCT/US2013/022136.
Thomas J. Flotte: "Pathology Correlations with Optical Biopsy Techniques", Annals of the New York Academy of Sciences, Wiley-Blackwell Publishing, Inc. SU, vol. 838, No. 1, Feb. 1, 1998, pp. 143-149.
Constance R. Chu et al: Arthroscopic Microscopy of Articular Cartilage Using Optical Coherence Tomography, American Journal of Sports Medicine, American Orthopedic Society for Sports Medicine, Waltham, MA, Vo. 32, No. 9, Apr. 1, 2004.
Bouma B E et al: Diagnosis of Specialized Intestinal Metaplasia of the Esophagus with Optical Coherence Tomography, Conference on Lasers and Electro-Optics. Technical Digest. OSA, US, vol. 56, May 6, 2001.
Shen et al: "Ex Vivo Histology-Correlated Optical Coherence Tomography in the Detection of Transmural Inflammation in Crohn's Disease", Clinical Gastroenterology and Heptalogy, vol. 2, No. 9, Sep. 1, 2004.
Shen et al: "In Vivo Colonscopic Optical Coherence Tomography for Transmural Inflammation in Inflammatory Bowel Disease", Clinical Gastroenterology and Hepatology, American Gastroenterological Association, US, vol. 2, No. 12, Dec. 1, 2004.
Ge Z et al: "Identification of Colonic Dysplasia and Neoplasia by Diffuse Reflectance Spectroscopy and Pattern Recognition Techniques", Applied Spectroscopy, The Society for Applied Spectroscopy, vol. 52, No. 6, Jun. 1, 1998.
Elena Zagaynova et al: "Optical Coherence Tomography: Potentialities in Clinical Practice", Proceedings of SPIE, Aug. 20, 2004.
Westphal et al: "Correlation of Endoscopic Optical Coherence Tomography with Histology in the Lower-GI Tract", Gastrointestinal Endoscopy, Elsevier, NL, vol. 61, No. 4, Apr. 1, 2005.
Haggitt et al: "Barrett's Esophaagus, Dysplasia, and Adenocarcinoma", Human Pathology, Saunders, Philadelphia, PA, US, vol. 25, No. 10, Oct. 1, 1994.
Gang Yao et al. "Monte Carlo Simulation of an Optical Coherence Tomography Signal in Homogenous Turbid Media," Physics in Medicine and Biology, 1999.
Murakami, K. "A Miniature Confocal Optical Scanning Microscopy for Endscopes", Proceedings of SPIE, vol. 5721, Feb. 28, 2005, pp. 119-131.
Seok, H. Yun et al: "Comprehensive Volumetric Optical Microscopy in Vivo", Nature Medicine, vol. 12, No. 12, Jan. 1, 2007.
Baxter: "Image Zooming", Jan. 25, 2005, Retrieved from the Internet.

(56) References Cited

OTHER PUBLICATIONS

Qiang Zhou et al: "A Novel Machine Vision Application for Analysis and Visualization of Confocal Microscopic Images" Machine Vision and Applications, vol. 16, No. 2, Feb. 1, 2005.

Igor Gurov et al: (2007) "Full-field High-Speed Optical Coherence Tomography System for Evaluting Multilayer and Random Tissues", Proc. of SPIE, vol. 6618.

Igor Gurov et al: "High-Speed Signal Evaluation in Optical Coherence Tomography Based on Sub-Nyquist Sampling and Kalman Filtering Method" AIP Coherence Proceedings, vol. 860, Jan. 1, 2006.

Groot De P et al: "Three Dimensional Imaging by Sub-Nyquist Sampling of White-Light Interferograms", Optics Letters, vol. 18, No. 17, Sep. 1, 1993.

Silva et al: "Extended Range, Rapid Scanning Optical Delay Line for Biomedical Interferometric Imaging", Electronics Letters, IEE Stevenage, GB vol. 35, No. 17, Aug. 19, 1999.

\* cited by examiner

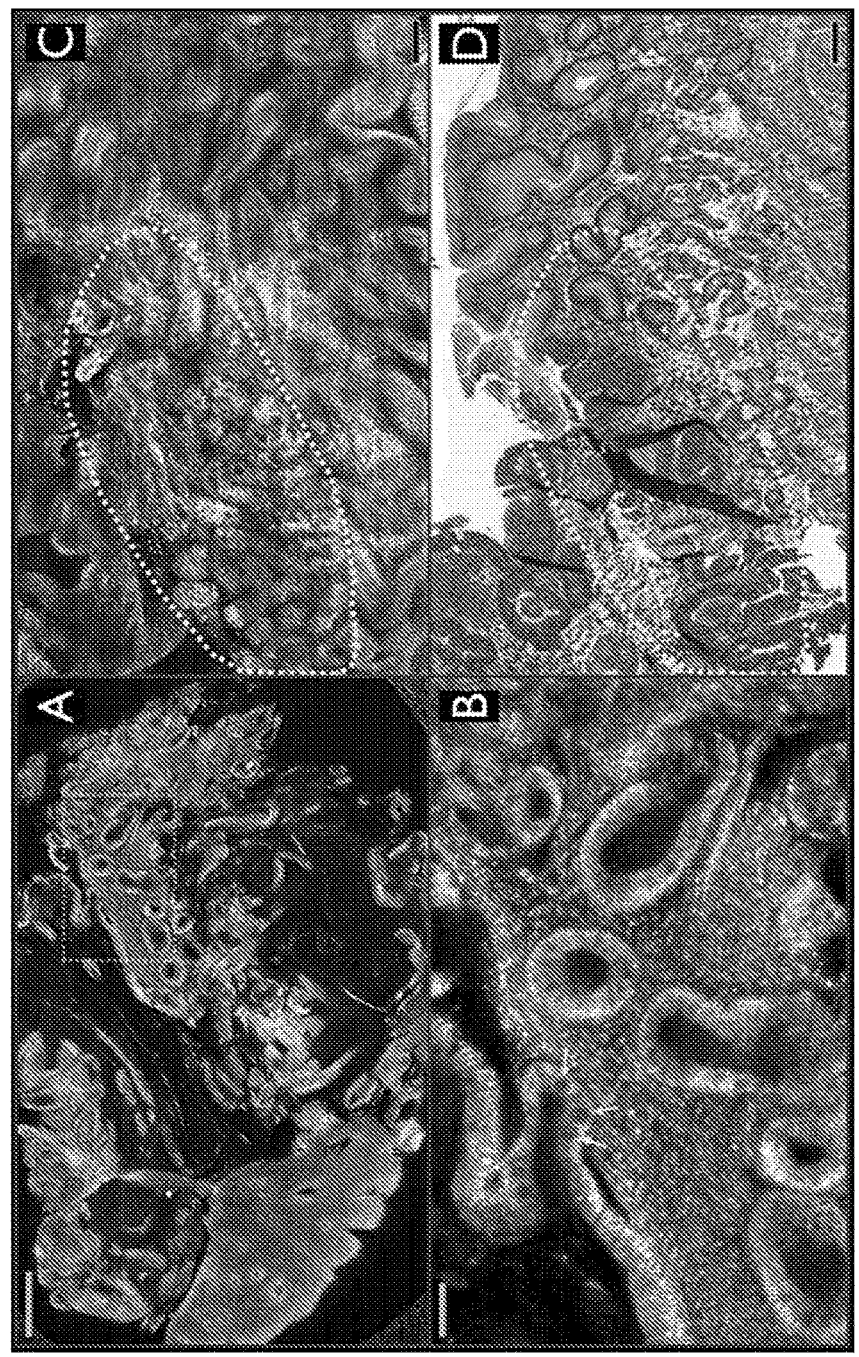

ENDOSCOPIC BIOPSY APPARATUS, SYSTEM AND METHOD

CROSS-REFERENCE TO RELATED APPLICATION(S)

This application is based upon and claims the benefit of priority from U.S. Patent Application Ser. No. 61/145,914, filed on Jan. 20, 2009, and from U.S. Patent Application Ser. No. 61/184,180, filed on Jun. 4, 2009, the entire disclosures of which are incorporated herein by reference.

STATEMENT REGARDING FEDERALLY SPONSORED RESEARCH

The invention was made with the U.S. Government support under Grant Nos. CA122161, RR019768 and EY014975 awarded by the National Institutes of Health and Grant No. W81XWH-07-2-0011 awarded by the U.S. Army Medical Research. Thus, the U.S. Government has certain rights in this invention.

FIELD OF THE DISCLOSURE

The present disclosure relates to exemplary embodiments of endoscopic biopsy systems that are guided by microscopic image information, and an associated method therefor.

BACKGROUND INFORMATION

The standard of care for the diagnosis of many epithelial precancerous and early cancer conditions is visual inspection of the patient directly or through an endoscope/laparoscope to identify abnormal tissue. Biopsies can then be obtained from these locations, processed, cut and stained with Hematoxylin and Eosin (H&E), and then observed under a microscope by a pathologist. A pathologist can view the slide at progressively increasing resolutions and renders a diagnosis by comparing its architectural and cellular patterns with his/her knowledge of patterns associated with different disease states.

For a number of cases, however, metaplasia, dysplasia, and early cancer may not be visually identified. In these situations, the only available option may be to obtain biopsies at random locations which are routinely conducted in the colon, esophagus, prostate, and bladder, among others. When the disease is focal or heterogeneously distributed within a much larger suspect area, a random biopsy procedure may be analogous to "finding a needle in a haystack," resulting in poor diagnostic yields and uncertain patient management.

Since random biopsies may only facilitate the assessment of less than 0.1% of the potentially involved tissue, these procedures are usually fraught with significant sampling error and diagnostic uncertainty. Other tasks, such as the delineation of surgical tumor margins, can also be affected by this difficulty, resulting in all too frequent re-excisions or time-consuming frozen section analysis. Thus, there may be a need for providing an apparatus and a method for guiding biopsy that is superior to visual inspection and that can direct the physician to a location that is more likely to harbor the most severe disease.

Barrett's esophagus is a condition of the tubular esophagus, where the squamous epithelium changes to intestinal epithelium, termed specialized intestinal metaplasia (SIM). Thought to be precipitated by severe or longstanding gastroesophageal reflux disease (GERD), BE can undergo dysplastic progression, leading to esophageal adenocarcinoma. Current management of Barrett's esophagus can include endoscopic surveillance at regular time intervals, consisting of upper endoscopy with 4-quadrant random biopsy, to identify dysplasia or adenocarcinoma at an early stage. This method suffers from a low sensitivity, as it is compromised by the poor ability of endoscopists to identify SIM/dysplasia and the low fractional area of tissue sampled by biopsy.

In the past, in the field of biomedical optics, imaging methods have been developed to provide improved tissue diagnosis in vivo. These imaging methods can be generally categorized as macroscopic or microscopic techniques.

Macroscopic, e.g., wide field imaging methods including autofluorescence, fluorescence lifetime imaging, ALA-fluorescence, reflectance and absorption spectroscopic imaging, narrow-band imaging, and chromoendoscopy. These macroscopic methods can be used to quickly evaluate large regions of tissue. While many of these techniques are promising, the information provided is often quite different from that conventionally used in medicine for diagnosis.

Microscopic imaging, at times referred to as "optical biopsy," is another approach that enables the visualization of tissues at a resolution scale that is more familiar to physicians and pathologists. In the past, the minimally-invasive endoscopic microscopy techniques that have been developed to visualize the architectural and cellular morphology required for histopathologic diagnosis in vivo facilitate a very small field of view, however, and the probes are usually manually manipulated to obtain images from discrete sites ("point-sampling"). As a result, such techniques suffer from substantially the same sampling limitations as excisional biopsy, and may not be well suited for guiding biopsy.

One such microscopic imaging technique, reflectance confocal microscopy (RCM), can be suited for non-invasive microscopy in patients as it offers imaging of cellular structures at ~1 µm resolution, can measure microstructure without tissue contact, and does not require the administration of unapproved exogenous contrast agents.

RCM can reject or ignore multiply scattered light from tissue, and detects the singly backscattered photons that contain structural information by employing confocal selection of light reflected from a tightly focused beam. Most commonly, RCM can be implemented by rapidly scanning a focused beam in a plane parallel to the tissue surface, resulting in transverse or en face images of tissue. A large numerical aperture (NA) of RCM can yield a very high spatial resolution. Sensitive to the aberrations that arise as light propagates through inhomogeneous tissue; high-resolution imaging with RCM can typically be limited to a depth of 100-200 µm, which is sufficient for most epithelial disorders that manifest near a luminal surface.

While RCM has been demonstrated in the skin, the development of endoscopic confocal microscopy systems has taken longer due to technical challenges associated with miniaturizing a scanning microscope. One difficulty with such technique is providing a mechanism for rapidly raster-scanning the focused beam at the distal end of a small-diameter, flexible probe. A variety of approaches have been attempted to address this problem, including the use of distal micro electro mechanical systems (MEMS) beam scanning devices, and proximal scanning of single-mode fiber bundles.

Another challenge can be the miniaturization of high NA objectives used for optical sectioning. Possible solutions employing a gradient-index lens system, dual-axis objectives or custom designs of miniature objectives have been described. First, demonstrations of these technologies in patients are beginning to appear; detailed images of the morphology of cervical epithelium have been obtained in vivo using a fiber optic bundle coupled to a miniature objective lens and fluorescence based images of colorectal and esophageal lesions were shown using commercial instruments.

Even though endoscopic RCM has been demonstrated in patients, this technique is likely not currently optimized for biopsy guidance. One reason can be that such technique provides microscopic images only at discrete locations, the so-called "point sampling" approach problem mentioned above. Point sampling is inherent to RCM since it has an extremely limited field of view (e.g., 200-500 µm), which is less than that of an excisional biopsy. As a result, endoscopic RCM may likely have the same sampling errors and diagnostic yield limitations as excisional biopsy.

In order to use endoscopic RCM for biopsy guidance, the imaging paradigm may be shifted away from point sampling to microscopy with extremely large fields of view where every possible location within the tissue of interest is sampled. The output of this paradigm, which can be termed "Comprehensive Volumetric Microscopy (CVM)," can include microscopic images of entire organ or luminal surfaces in three-dimensions.

For CVM, imaging speeds of current techniques may need to be increased by at least an order of magnitude above video rate, due to the very high bandwidth of the microscopic information and the constraint of obtaining such data in a realistic procedural time (e.g., <20 min). In addition, catheter/endoscope technology can be developed to automatically scan the microscope over these large tissue surface areas rapidly and with a high degree of precision.

Recently, CVM has been implemented using a second-generation form of optical coherence tomography (OCT), called optical frequency domain imaging (OFDI), and rapid helically scanning catheters. This research has facilitated the acquisition of three-dimensional microscopic images of the entire distal esophagus in a few minutes and long segments of coronary arteries in patients in less than 5 seconds. (See Suter M. J. et al., "Comprehensive microscopy of the esophagus in human patients with optical frequency domain imaging", Gastrointestinal endoscopy, 2008, Vol. 68(4), pp. 745-53; and Tearney G. J. et al., "Three-dimensional coronary artery microscopy by intracoronary optical frequency domain imaging: First-in-human experience", Journal of the American College of Cardiology, Imaging, 2008, pp. 1:752-61

While OFDI shows significant potential for certain clinical applications, its ~10 µm resolution may not necessarily be sufficient for dysplasia and early cancer diagnosis, which can require knowledge of tissue morphology at both architectural and cellular levels. Thus, there may be a need to provide a new exemplary variant of RCM that is capable of rapidly obtaining high-resolution comprehensive volumetric images through an endoscopic probe.

One approach is to use spectrally encoded microscopy ("SECM") technique(s). SECM's rapid imaging rate and its fiber-optic design can enable comprehensive volumetric RCM through an endoscopic probe. An SECM probe has been described which can scan an area equivalent to that of the distal esophagus (about 5.0 cm length, and about 2.5 cm diameter), at a single depth location, in approximately 1 minute. (See, e.g., Yelin D. et al., "Large area confocal microscopy", Optics Letters, 2007; 32(9):1102-4).

Spectrally encoded confocal microscopy ("SECM") is a single fiber-optic confocal microscopy imaging procedure, which uses a broad bandwidth light source and encodes one dimension of spatial information in the optical spectrum (as illustrated in the example of FIG. 1). As shown in FIG. 1, at the distal end of the probe, the output from the core of a single-mode or dual-clad fiber 110 is collimated by a collimation lens 115 and illuminates a transmission diffraction grating 120. An objective lens 130 focuses each diffracted wavelength to a distinct spatial location 141, 142, or 143 within the specimen, producing a transverse line focus 150 where each point on the line has a different wavelength or color. After reflection from the tissue, the light passes back through the lens 130, is recombined by the grating 120, and collected by the fiber 110. The aperture of the fiber 110 provides the spatial filtering mechanism to reject out-of-focus light. Outside the probe (within the system console) the spectrum of the returned light is measured and converted into confocal reflectance as a function of transverse displacement within the sample. Spectral decoding of this line in the image can be performed very rapidly, e.g., at rates of about 70 kHz, which can be approximately 10 times that of video rate confocal microscopy systems and up to about 100 times faster than some endoscopic RCM systems. The other transverse axes of the image can be obtained by relatively slow and straightforward mechanical actuation that may regularly employ for a wide variety of endoscopic probes. Images obtained by SECM demonstrate its capability to image subcellular-level microstructure relevant to the diagnosis of dysplasia and cancer (see FIG. 2). FIGS. 2A and 2B show exemplary SECM images of swine duodenum, obtained ex vivo, after compression of the bowel wall, showing the architecture of the duodenal villi and nuclear detail. Illustrated imaging depths are 50 µm and 100 µm shown in FIGS. 2A and 2B, respectively.

Accordingly, there may be a need to overcome at least some of the above-described issues and/or deficiencies.

SUMMARY OF EXEMPLARY EMBODIMENTS

Thus, at least some of these issues and/or deficiencies can be addressed with the exemplary embodiments of the apparatus, system and method according to the present disclosure.

Exemplary embodiments of the present disclosure provides mechanism and a methodology for automatically maintaining the foci at a desired tissue depth while scanning the spectrally encoded line across the sample. This exemplary advancement can compensate for patient motion and enables imaging at multiple depth locations. Further, in one exemplary embodiment, it is possible to conduct a large area confocal microscopy in patients by incorporating these technologies in an endoscopic probe suitable for human use.

According to another exemplary embodiment of the present disclosure, an apparatus can be provided. The apparatus can comprise at least one dispersive first arrangement which is configured to provide data associated with a signal received from at least one region of the sample(s). The exemplary apparatus can also comprise at least one focusing second arrangement which is configured to control a focal length and/or a focal position associated with first arrangement based on the data. According to an exemplary variant, at least one third arrangement can also be availed which is configured to provide further data associated with a further signal received from at least one further region of at least one sample. The region and the further region can at least partially overlap and/or be located at near one another. The focusing second arrangement(s) can be configured to control the focal length and/or the focal position associated with the first arrangement(s) based on the data and/or the further data. The dispersive and focusing arrangements can be provided in a balloon.

According to a further exemplary embodiment of the present disclosure, apparatus, method and system can be provided for imaging at least one portion of an anatomical tissue can also be provided. For example, with a dispersive arrangement, it is possible to provide at least one first electromagnetic radiation to the at least one portion to form a sample plane at an angle that is greater than 0 degrees and less than 90 degrees with respect to a plane of a surface of the portion(s). Further, at least one second electromagnetic radiation can be received from the sample plane which is associated with the first electromagnetic radiation(s) to generate information as a function the second electromagnetic radiation(s). A control signal can be generated based on the information so as to further control a location of a focal plane of the first electromagnetic radiation(s), or at least one three-dimensional image of the at least one portion can be generated as a function of the information.

In one exemplary variant, it is possible to generate the control signal based on a location of a surface of the sample using at least one portion of the at least one first electromagnetic radiation. It is also possible to separate the second electromagnetic radiation(s) into at least one first signal and at least one second signal. Further, the control signal can be generated based on the first signal(s), and at least one image associated with the sample can be generated as a function of the second signal(s).

In a further exemplary embodiment of the present disclosure, the SECM probe components can be incorporated into a transparent tube, e.g., having about 1.0 cm in diameter, with an approximately 2.5 cm diameter centering balloon and a rapid-exchange guide wire provision. Helical scanning can be accomplished by the use of a rotary junction and a pullback motor connected to the SECM optics via a wound cable through the tube. An exemplary arrangement in which an objective lens is angled relative to the surface of the sample can be used. This angled arrangement can be used to generate a feedback signal for controlling the focal plane of the objective lens and also provide three-dimensional image information through a single helical scan. The transverse resolution of the SECM optics can be, e.g., nominally about 1.6 μm and the autofocus mechanism can function, e.g., over a range of about ±500 μm. The SECM imaging system, operating at a center wavelength of 725 nm and capable of configured to obtain image data at about $70\times10^6$ pixels per second, can be enclosed in a portable arrangement, e.g., a cart.

The exemplary system and probe can be configured to comprehensively image the entire human distal esophagus (about 2.5 cm diameter and about 5.0 cm length) at about 10 different focal locations, in approximately 10 minutes. Exemplary software can be provided and stored on a tangible computer-accessible medium (and executed by a processor or other computing arrangement(s)) a for convenient image data acquisition, display, and selection of sites to be marked for biopsy.

In yet another exemplary embodiments of the present disclosure, a laser marking apparatus, method and system can be provided according to the present disclosure. An approximately 400 mW, 1450 nm laser can be incorporated into the system and coupled into an endoscopic probe to create minute, visible superficial marks on tissue at selected image locations so that they may be subsequently biopsied by the endoscopist. For example, target sites, identified by SECM or OCT, can be marked so that the endoscopist can review and biopsy these locations. An exemplary embodiment of a laser marking apparatus, method and system can be provided for accomplishing this exemplary task. The exemplary laser marking technique can be incorporated into the exemplary embodiment of the apparatus, system and device according to the present disclosure.

According to one exemplary embodiment of the present disclosure, apparatus, method and system can be provided for determining a position on or in a biological tissue can be provided. For example, using such exemplary embodiment, it is possible (using one or more arrangements) to receive information associated with at least one image of at least one portion of the biological tissue obtained using an optical imaging technique. Further, it is possible to, based on the information, cause a visible change on or in at least location of the portion(s) using at least one electro-magnetic radiation.

For example, the image(s) can include a volumetric image of the portion(s). The volumetric image can be a cylindrical image having a diameter of between about 10 mm to 100 mm and/or an extension of at most about 1 m. It is also possible (e.g., using a particular arrangement) to receive data associated with the visible change, and guide a visualization to the at least one portion based on the data. Further, it is possible to cause the visible change by ablating the portion(s). The ablation can be performed by irradiating the portion(s) with the electro-magnetic radiation(s).

In one exemplary embodiment of the present disclosure, the arrangement can be situated in a probe, and an ablation arrangement can be provided in the probe which is controlled by the arrangement to cause the visible change on or in one or more the portions. It is also possible to obtain the information via at least one wave-guiding arrangement, and the ablation arrangement can provides the electro-magnetic radiation(s) via the wave-guiding arrangement(s) to cause the visible change. In addition, the optical imaging technique can include a confocal microscopy technique, and the confocal microscopy technique can be a spectrally-encoded confocal microscopy technique. Further, the optical imaging technique can include an optical coherence tomography.

These advancements can achieve performance specifications that can be used for endoscopic use in patients. It is also possible to incorporate exemplary embodiments described herein in an endoscope and utilize the targeted biopsy technique, e.g., in clinical studies and in other scenarios.

The exemplary embodiment of the system and probe according to the present disclosure described herein can be used in patients undergoing upper endoscopy. While the application of the exemplary embodiments can be to a wide variety of epithelial cancers and other clinical applications such as tumor margin detection, one exemplary application can be for Barrett's esophagus (BE), as it is an area where these exemplary embodiments may have a high impact. Because the exemplary comprehensive SECM can sample the entire distal esophagus on a microscopic scale, the exemplary SECM-guided biopsy can yield a significantly higher sensitivity for the detection of dysplasia and early adenocarcinoma.

According to the exemplary embodiments of the present disclosure, it is possible to screening patients for Barrett's esophagus and improving the diagnostic capabilities of surveillance endoscopy. These advances can decrease the mortality associated with esophageal adenocarcinoma.

The image-guided biopsy according to the exemplary embodiments of the present disclosure is expected to be safe and well-tolerable, detect previously unattainable subcellular and architectural information over large epithelial surfaces of the esophagus, and provide an effective method for endoscopic biopsy targeting. The impact of these exemplary embodiments can be high, as it can provide clinicians with a powerful tool for improving the management of BE patients. While the broad goal of this invention is focused on reducing the mortality of esophageal adenocarcinoma, the exemplary SECM system and probe represent a new diagnostic platform that can be applied to dysplasia and cancer screening in other internal organ systems. The long term impact of the exemplary embodiments of the present disclosure can also affect treatment as it can enable less invasive surgical techniques such as RF ablation, photodynamic therapy, or endoscopic mucosal resection to be used at an earlier stage of disease progression.

According to the exemplary embodiments of the present disclosure, it is possible to screening patients for Barrett's esophagus and improving the diagnostic capabilities of surveillance endoscopy. These advances can decrease the mortality associated with esophageal adenocarcinoma.

To utilize comprehensive SECM to guide biopsy, additional exemplary procedures and/or steps can be taken. As an initial matter, the images are interpreted during the procedure. A comparison of SECM images of biopsy samples to corresponding histology can be performed that can describe an exemplary criteria for SECM diagnosis. Another exemplary embodiment of the system, device and method according to the present invention can be provided for obtaining information that is compatible with current morphologic methods for disease diagnosis. Advantages of this exemplary embodiment can include near-term clinical application and the potential for leveraging a large, existing database of clinic pathologic correlations. Further, it is likely that molecular imaging provide an impact in changing this paradigm in the future.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 9A is an exemplary SECM image of a specialized intestinal metaplasia obtained using the exemplary embodiment of the system and method according to the present disclosure was acquired following application of 0.6% acetic acid;

FIG. 9B is a magnification view of the image of FIG. 9A showing goblet cells;

FIG. 9C is an exemplary SECM image of a high grade dysplasia obtained using the exemplary embodiment of the system and method according to the present disclosure;

FIG. 9D is an exemplary SECM image according to the exemplary embodiments of the present disclosure demonstrating architectural and nuclear atypia;

DETAILED DESCRIPTION OF EXEMPLARY EMBODIMENTS

Exemplary embodiments of the systems, processes and arrangements according to the present disclosure includes, but not limited to (a) a SECM endoscopic probe, (b) diagnosis based on histopathologic features observed in SECM images, and/or (c) an image-guided laser marking system, etc. A description of each of these three exemplary embodiments is described in detail below, along with an exemplary embodiment of a clinically-viable SECM-guided biopsy system/probe according to the present disclosure.

Exemplary SECM Probe

Figure 1:
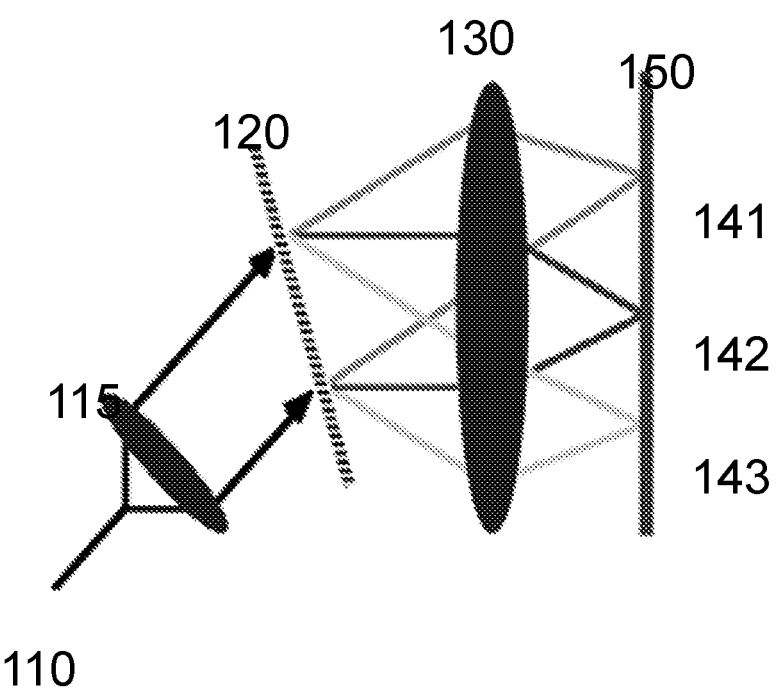
FIG. 1 is a schematic diagram of an exemplary arrangement which utilizes spectrally-encoded confocal microscopy (SECM) techniques.
Figures 2A, 2B:
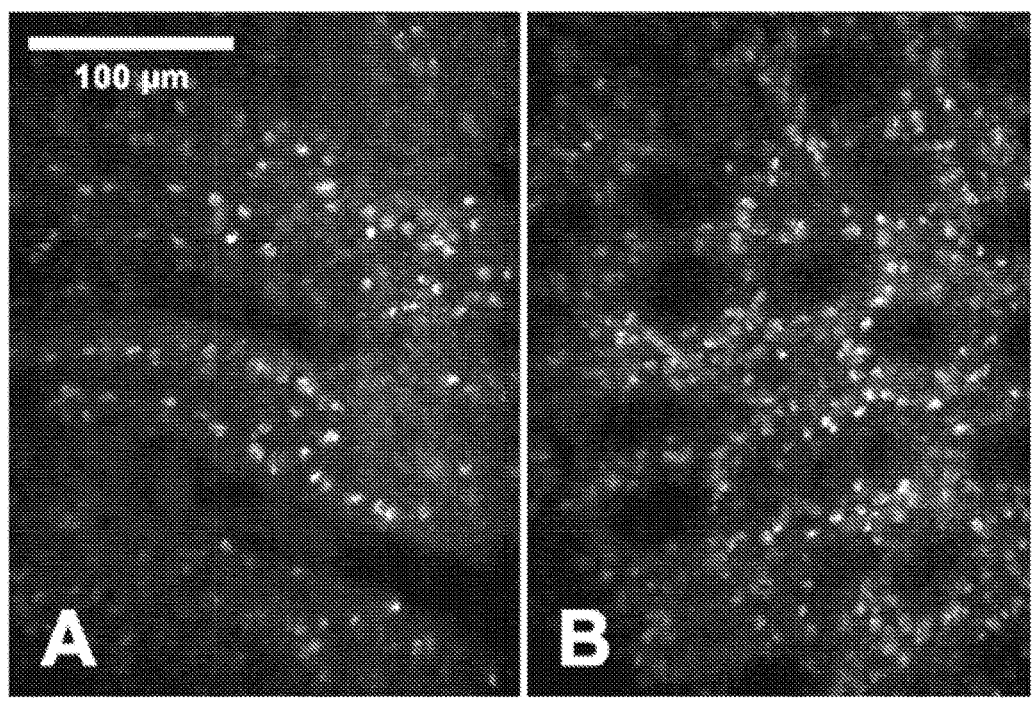
FIG. 2A is a SECM image of swine duodenum, obtained ex vivo, after compression of the bowel wall using the exemplary arrangement illustrated in FIG. 1 showing the architecture of the duodenal villi and nuclear detail at an imaging depth of about 50 µm.
FIG. 2B is another SECM image of swine duodenum, obtained ex vivo, after compression of the bowel wall using the exemplary arrangement illustrated in FIG. 1 showing the architecture of the duodenal villi and nuclear detail at an imaging depth of about 100 µm.
Figure 3:
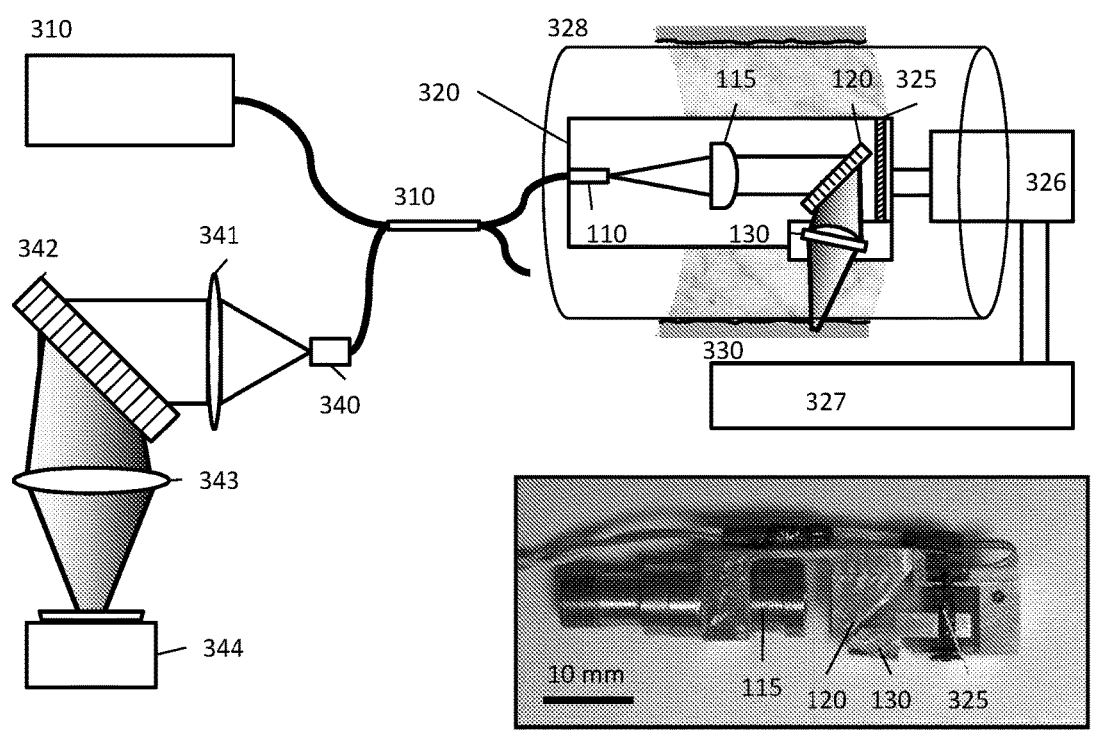
FIG. 3 is a schematic diagram and a photograph inset of an exemplary SECM arrangement/probe according to an exemplary embodiment of the present disclosure.

Exemplary embodiments of the present disclosure which include certain arrangement/probe components facilitate comprehensive endoscopic SECM imaging of large luminal surfaces can be provided. As shown in the exemplary embodiment illustrated in FIG. 3, light from a broadband light source 310 (e.g., spectral bandwidth=about 30 nm; central wavelength=about 877 nm) can be coupled into a 50/50 fiber-optic beam splitter 320. Light from the fiber output port 110 of the beam splitter can be collimated by a collimation lens 115 (e.g., f=about 20 mm), and dispersed by a transmission holographic grating 120 (e.g., about 1700 lines/mm) into e.g., ~350 resolvable points. The dispersed light can be focused onto the specimen 330 by an objective lens 130 (e.g., aspheric lens: f=about 4.5 mm; effective NA=about 0.53) through a thin-walled balloon 328 (e.g., diameter=about 20 mm; thickness=about 50 µm). The objective lens 130 can be angled so that the axial positions of the focused spots vary by e.g., about 50 µm across the imaging bandwidth. Helical scanning can be accomplished by rotating and translating the probe housing 320 by a motor 326 and a translation stage 327. A photo of the exemplary embodiment of the SECM probe is shown in the inset of FIG. 3. The size of the exemplary probe can be about 10 mm (W)×39 mm (L)×13 mm (H). The reflected light can be coupled back into the beam splitter and directed to a spectrometer comprising a collimation lens 341 (f=about 44 mm), a grating 342 (about 1800 lines/mm), a focusing lens 343 (f=about 200 mm), and a line scan camera 344 (e.g., Basler Sprint; pixel size=about 10 µm; 2048 pixels). The exemplary spectral resolution of the spectrometer can be about 0.04 nm.

To generate depth-resolved optical sections, each digitized spectrally-encoded line can be divided into, e.g., 8 segments where each segment corresponds to image information obtained at a different depth level. Exemplary image segments from the same depth level can be connected together to create a large-area optical section at each depth. In order to keep the focus of the high NA objective lens 130 within the sample 330, the objective lens 130 can also be scanned along the axial direction by a focusing mechanism 325, which can include a miniature linear guide and a piezoelectric transducer (PZT) actuator.

Figure 4:
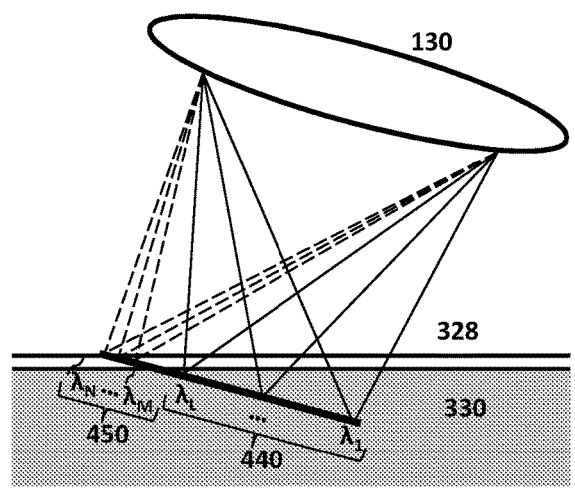
FIG. 4 is a schematic diagram of an exemplary spectrally encoded illumination on tissue using the exemplary embodiment of the arrangement/probe shown in FIG. 3.
Figure 5A:
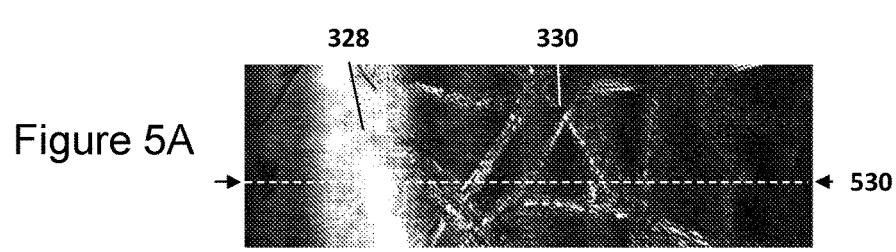
FIG. 5A is an exemplary SECM image which can be utilized for focusing by the exemplary embodiment of the arrangement according to the present disclosure.
Figure 5B:
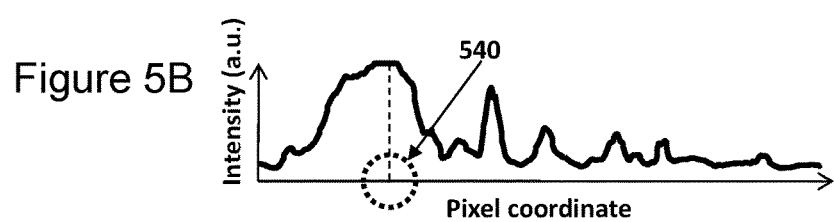
FIG. 5B is an exemplary graph of intensity versus pixel coordinate associated with the exemplary SECM image shown in FIG. 5A.

FIG. 4 shows a schematic diagram of the illumination beam from the objective lens 130 on the sample 330 through the balloon 328. Since the objective lens 130 is angled, each wavelength can image at a different depth of the sample 330. A spectral band 450 that images the balloon region 328 at a line scan can be used to locate the balloon surface in the field of view, which can be used to generate a feedback signal to control the focusing mechanism 325. for example, the remaining spectral band 440, together with the spectral band 450, can be used to generate line image of the sample 330. FIG. 5A shows an exemplary image that can be generated by the exemplary embodiment of the SECM arrangement/probe according to the present disclosure as shown in FIGS. 3 and 4. For example, the portion that visualizes the balloon 328 has higher signal level than that for the sample 330. The line profile along a line 530 (shown in FIG. 5B) illustrates a high intensity peak 540 at the balloon location, and such peak location can be used as a reference point to control the focusing mechanism (e.g., using a processing or computing device or arrangement).

Exemplary Experimental Results

The transverse resolution of the exemplary embodiment of the SECM arrangement/probe according to the present disclosure, measured by imaging the edge response function from bars on a 1951 USAF resolution chart, ranged from 1.25±0.13 µm to 1.45±0.33 µm, from the center to the edges of the spectral field of view, respectively. The axial resolution of the exemplary embodiment of the SECM arrangement/probe, obtained by z-scanning a mirror through the focus, was measured to be 10 µm and 4.4 µm for the edge and the center of the spectral FOV's, respectively. The adaptive focusing mechanism in the exemplary embodiment of the SECM arrangement/probe accurately tracked the sinusoidal motion of a moving mirror at rate of 1 Hz with displacement amplitude of about 250 µm. The exemplary mechanical design of the probe head and the software procedure used in this exemplary embodiment of the arrangement/probe was somewhat limited the speed and range of the adaptive focusing mechanism. It is possible to generate the feedback signal using a separate opto-electronic apparatus and it is possible to modify the probe housing, which can increase the response speed of the feedback loop and the focal range, respectively.

Figure 6A:
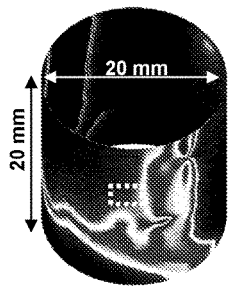
FIG. 6A is a cylindrical presentation of an exemplary image of a lens paper phantom obtained by an exemplary SECM bench-top probe without adaptive focusing.
Figure 6B:
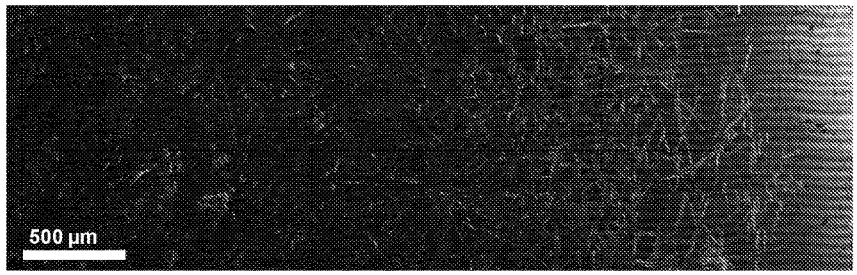
FIG. 6B is a magnified view of the exemplary image shown in FIG. 6A.
Figure 6C:
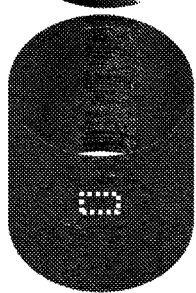
FIG. 6C is a cylindrical presentation of an exemplary image of the lens paper phantom obtained by the exemplary SECM bench-top probe with adaptive focusing.
Figure 6D:
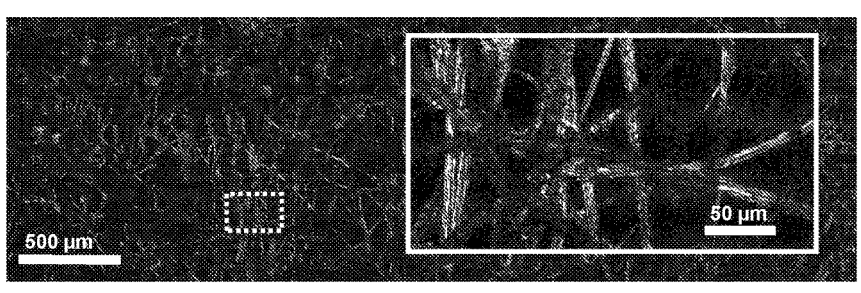
FIG. 6D is a magnified view of the exemplary image shown in FIG. 6C.

FIGS. 6A-6E show exemplary SECM images and data for a substantially complete exemplary pullback image of, e.g., a 2.0 cm phantom without adaptive focusing (see FIGS. 6A and 6B) and with adaptive focusing (see FIGS. 6C and 6D). The exemplary phantom consists of lens paper affixed to the outer surface of the balloon (diameter=about 20 mm). The exemplary embodiment of the SECM arrangement/probe according to the present disclosure was scanned using a rotation rate of about 20 rpm; a total of about 400 circumferential scans were acquired in 20 minutes, limited primarily by the speed of the method used to generate the control signal. Since the length of a single spectrally-encoded line was 400 µm, the longitudinal step size of 50 µm provided 8 different depth levels. At low magnification (shown in FIGS. 6A and 6C), the macroscopic structure of the paper, including folds and voids, can be visualized. When regions of this data set are shown at higher magnifications, individual fibers and fiber microstructure can be clearly resolved (as shown in FIGS. 6B and 6D—see inset).

Figure 6E:
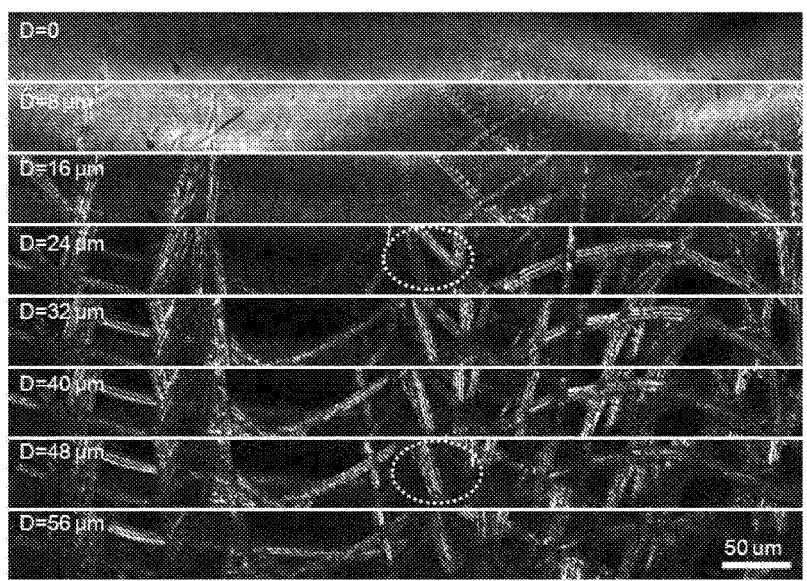
FIG. 6E is an illustration of an exemplary stack of SECM images of the lens paper phantom at a region of the sample over the imaging depth of 56 µm.

By utilizing the automatic focusing mechanism (the image produced by which is shown in FIGS. 6C and 6D), the entire dataset remained in focus and information can be acquired from all optical sections within the approximately 50 µm range, even when the exemplary arrangement/probe was not centered. In contrast, when the focusing mechanism was off, only small portions of the phantom were in focus and visible (as shown in FIGS. 6A and 6B). A stack of exemplary SECM images at a region of the sample through different imaging depths is shown in FIG. 6E. This exemplary image stack provides three-dimensional information over the depth of about 56 µm at 8 different focal planes. Feature changes are well noticed between the images from the different imaging planes including the white dotted circular region. These exemplary results demonstrate the technical feasibility of comprehensive exemplary SECM for luminal organs.

Histopathologic Features Visualized by Exemplary SECM Techniques

Figure 7:
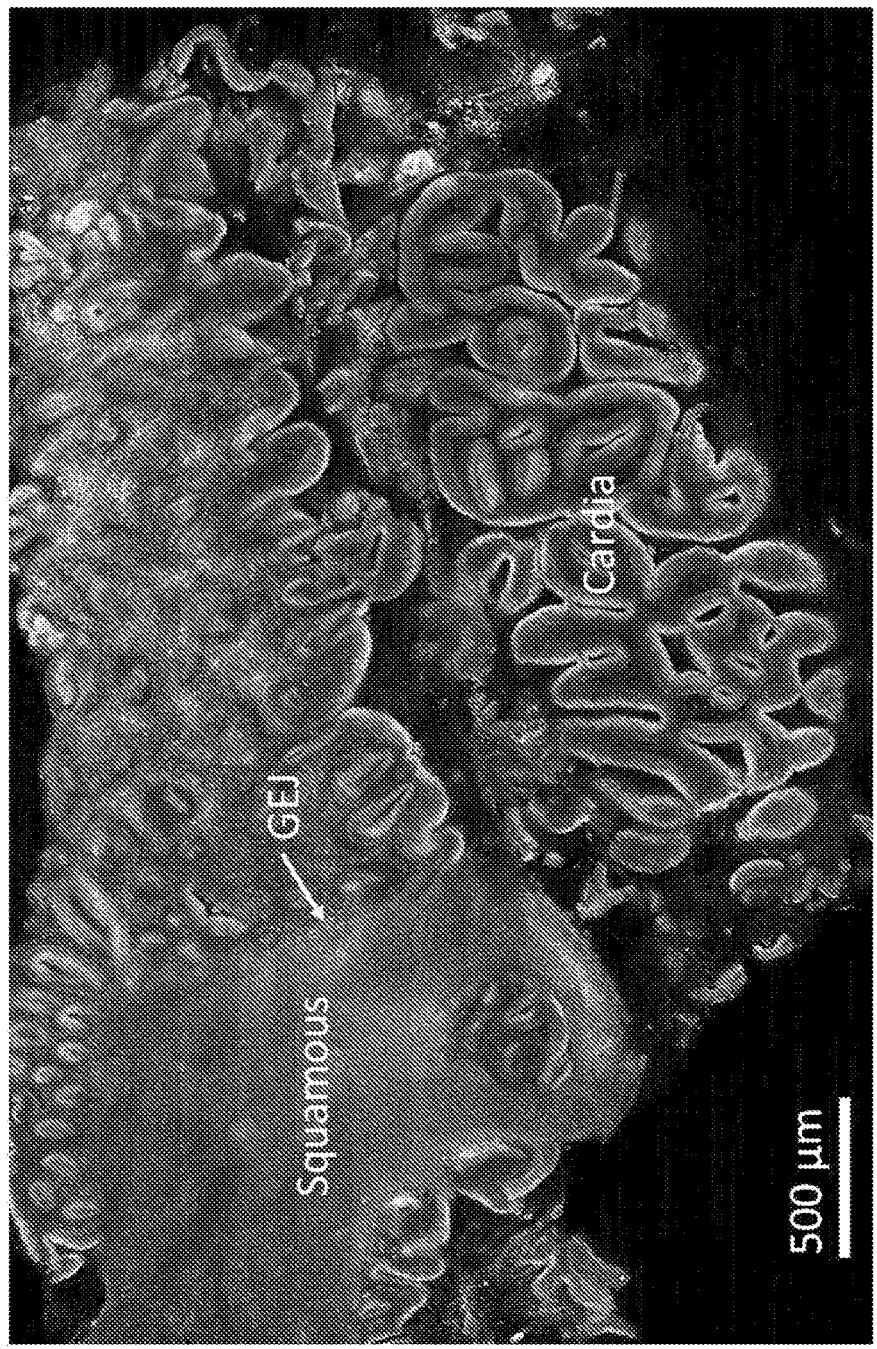
FIG. 7 is an exemplary SECM image of a human esophageal biopsy sample showing the gastroesophageal junction, squamous epithelium, and gastric cardia.

An exemplary SECM system with similar optical specifications as that described herein above for the exemplary embodiment of the endoscopic SECM probe can be utilized, e.g., to image entire human biopsy samples (as described in, e.g., Kang D. et al., "Comprehensive imaging of gastroesophageal biopsy samples by spectrally encoded confocal microscopy", Gastrointest Endosc. 2009). This exemplary SECM system can utilize a wavelength-swept source (e.g., central wavelength=1320 nm; bandwidth=70 nm; repetition rate=5 kHz) and a 0.7 NA objective lens. A single-mode illumination and multi-mode detection imaging configuration can be used to reduce laser speckle noise, a method that can also be employed in the exemplary arrangement/probe described herein above. The resolutions of such exemplary SECM system can be, e.g., 2.3 µm and 9.7 µm along the transverse and axial directions, respectively. FIG. 7 shows an exemplary image of one of the first data sets that have been acquired from an exemplary biopsy study, demonstrating the architectural morphology of, e.g., a normal gastroesophageal junction.

Figures 8A, 8B, 8C:
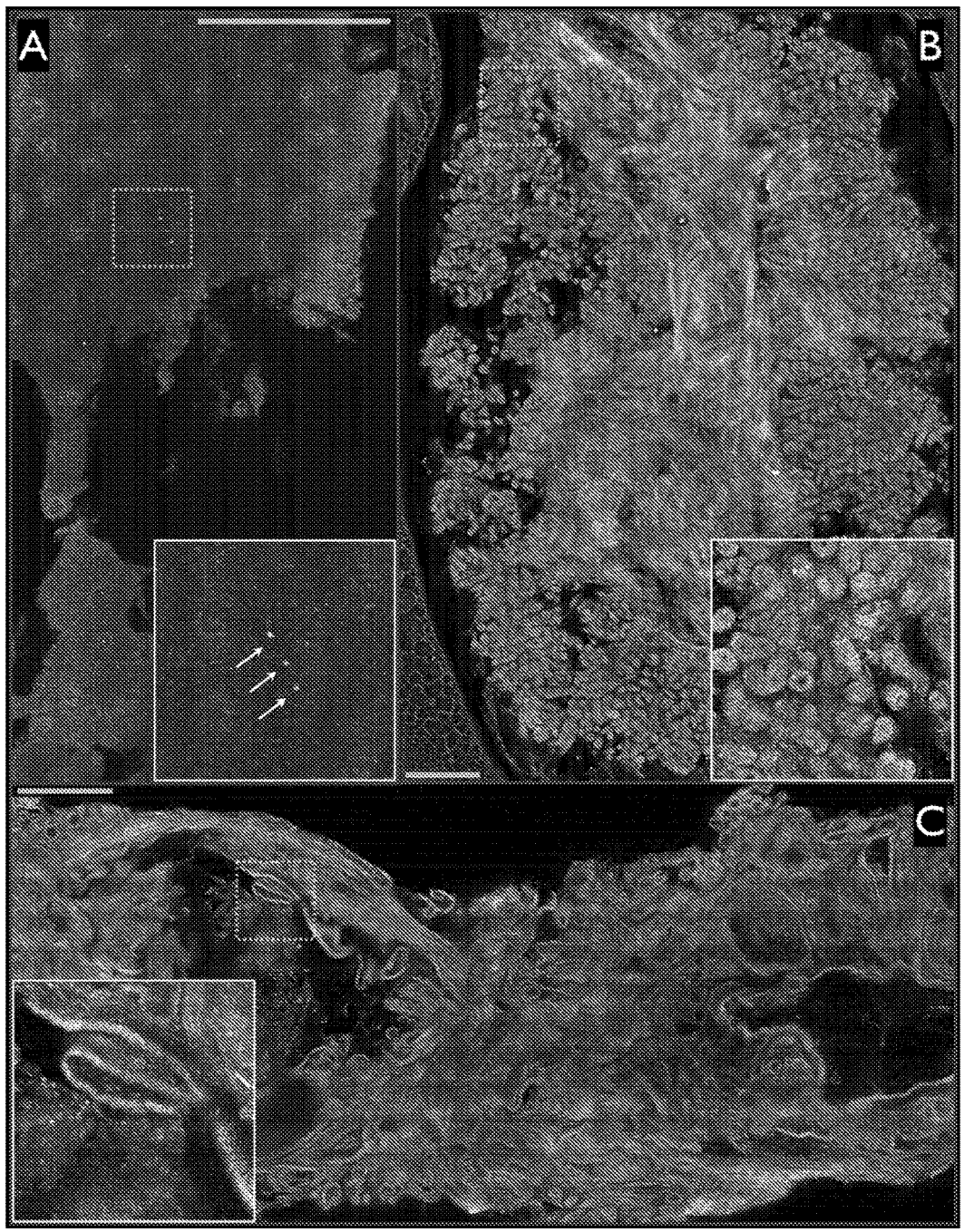
FIG. 8A is an exemplary SECM image of esophageal squamous epithelium showing intraepithelial eosinophils from a patient with presumed eosinophilic esophagitis.
FIG. 8B is an exemplary SECM image of a gastric body fundic type mucosa from the patient with presumed eosinophilic esophagitis imaged following 0.6% acetic acid.
FIG. 8C is an exemplary SECM image of Fundic gland polyp with columnar epithelium lining the cyst wall from the patient imaged following 0.6% acetic acid.

Exemplary SECM images of other esophageal tissue types can also be obtained, including squamous mucosa with scattered eosinophils gastric fundic body type mucosa and a fundic gland polyp (see FIGS. 8A, 8B and 8C). Images of Barrett's esophagus (see FIGS. 9A and 9B) appear to be distinct from gastric cardia (as shown in FIG. 7) and high-grade dysplasia (as shown in FIG. 9C). For example, an application of 0.6% acetic acid (vinegar) for enhancing nuclear contrast can be performed on, e.g., the majority of the biopsy samples. Further clinical study of SECM imaging on a larger set of biopsy samples can deliver diagnostic criteria of SECM imaging and evaluate its accuracy. The diagnostic criteria can be used in the SECM-guided biopsy to identify and locate diseased regions automatically or manually by clinicians or image readers.

Exemplary Laser Marking for Guiding Biopsy

To utilize endoscopic microscopy techniques to guide biopsy, regions of dysplasia and early carcinoma identified by the imaging system can be marked so that they can be visible by traditional endoscopy.

Figure 10:
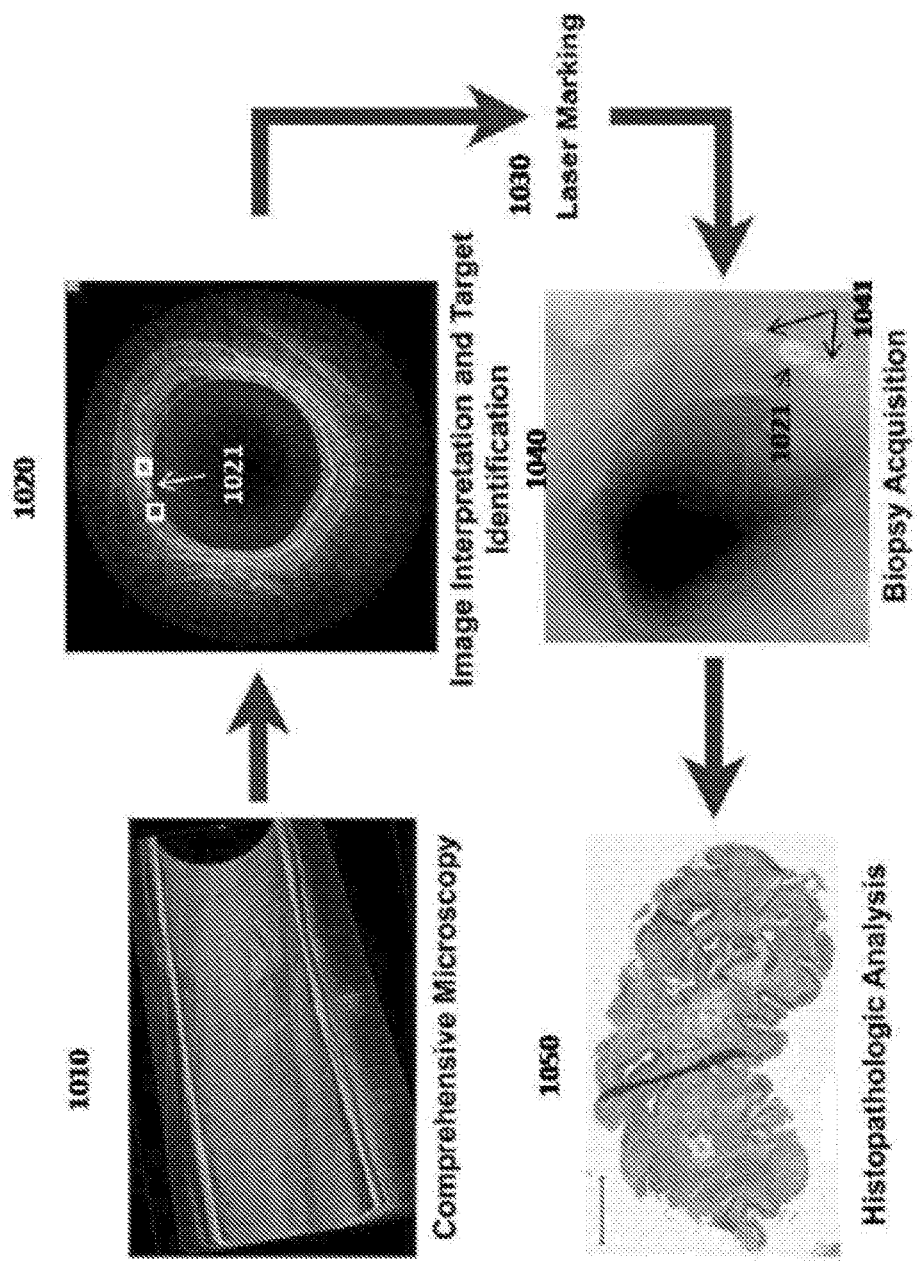
FIG. 10 is an exemplary image flow diagram of the comprehensive microscopy guided biopsy platform with laser marking according to an exemplary embodiment of the method of the present disclosure.

FIG. 10 shows an image progress diagram of an exemplary embodiment of a method of image-guided biopsy that uses laser marking of the superficial esophageal mucosa according to the present disclosure. To demonstrate the feasibility of laser marking targeted biopsy, this exemplary technique has been tested in swine in vivo (n=4) through a balloon catheter with OFDI imaging modality. For each animal, the balloon catheter and inner optical imaging probe were positioned within the esophagus. A 400 mW, 1450 nm laser was used to mark the esophagus through a fiber-optic probe, focused to a spot diameter of approximately 30 µm. A total of 68 randomly located 8-second targets 1021 were created in the swine esophagus. A comprehensive microscopy dataset 1010 of the distal 5.0 cm of the esophagus was then obtained and used 1020 to locate the targets 1021. After locating a target on the endoscopic microscopy image, smaller 2-second laser marks 1041 were made on either side of the target to serve as a guide for biopsy 1030 (see FIG. 10). Following laser marking, the balloon catheter was removed and the esophagus was visualized by conventional endoscopy 1040. An inspection of the esophagus 1040 revealed that both marks surrounding 1041 each target 1021 were visible by endoscopy for about 97% of the targets. Histopathological analysis 1050 of the marks showed that both the 8- and 2-second marks caused only minor injury to the mucosa, extending to the superficial submucosa, which healed after two days. These exemplary results demonstrate that laser marking is a viable approach for facilitating biopsy guided by endoscopic microscopy. Although OFDI imaging modality was used for this experiment, SECM can also be utilized through a balloon catheter to guide biopsy.

For various internal organ systems, random biopsy can be the standard of care for the diagnosis of epithelial metaplasia, dysplasia, and early cancer. SECM-guided biopsy can change this paradigm and improve outcomes for patients who undergo regular surveillance for these conditions. SECM may be capable of identifying architectural and cellular microstructure relevant to esophageal diagnosis. Certain exemplary technical components can be preferred for implementing SECM-guided biopsy in an endoscopic probe. It is possible to provide an exemplary embodiment of a clinically viable SECM system and endoscopic probe. The exemplary system/device can obtain RCM data at multiple depths over the entire distal esophagus, and can facilitate the physician to identify and mark suspect locations in the tissue so that they can be subsequently biopsied.

Exemplary SECM-Guided Biopsy

Figure 11:
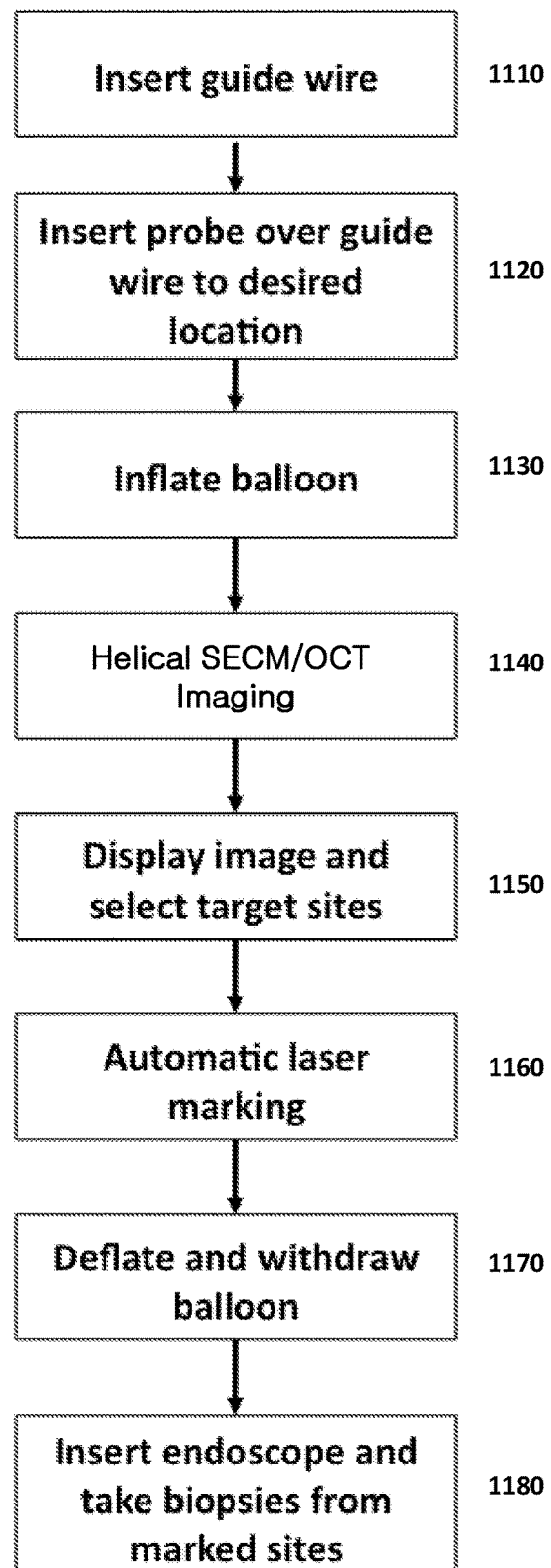
FIG. 11 is an exemplary flow diagram of the SECM-guided biopsy process according to an exemplary embodiment of the present disclosure.

FIG. 11 illustrates a flow diagram of exemplary embodiment of the procedures according to the present disclosure for conducting the exemplary SECM-guided biopsy. For example, a centering balloon probe can be inserted over a guide wire (block 1120) that has been previously placed endoscopically (block 1110). When the balloon probe is in place, the balloon can be inflated in block 1130, and comprehensive SECM can be performed using a helical scan pattern in block 1140. In the endoscopic suite, the exemplary SECM dataset can be analyzed, and biopsy targets may be selected on the image in block 1150. The SECM probe can then automatically return to those locations in the patient and can place laser marks on either side of the targets in block 1160. Following such exemplary laser marking, the balloon can be deflated and removed in block 1170. The endoscopist can then obtain biopsies from the marked sites in block 1180. Although SECM is used in the exemplary procedures shown in FIG. 11, other microscopic imaging technologies including OCT can be also used to guide the biopsy.

Exemplary Endoscopic Probe

Figure 12:
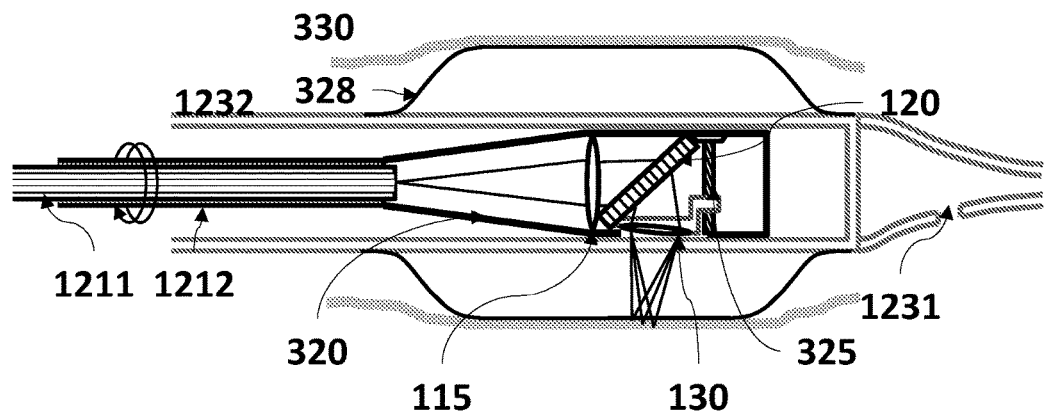
FIG. 12 is a schematic diagram of a side view of an exemplary SECM arrangement/probe according to an exemplary embodiment of the present disclosure.

A clinical exemplary SECM-guided biopsy device can comprise, e.g., three components: a) the probe, b) the probe-console interface, and c) the console. An exemplary schematic diagram of an exemplary embodiment of the SECM arrangement/probe is shown in FIG. 12. The exemplary SECM arrangement/probe can comprise a double-clad fiber (DCF) 1211 which can transceive the imaging light, and also transmit the laser marking beam. To reduce speckle noise, imaging can be accomplished by illuminating the sample through the core of the DCF, and by receiving the light remitted from the sample through both the core and inner cladding. The fiber can be contained within a wound cable 1212 that rotates, and can translate within a transparent 1.0 cm diameter sheath 1232.

Rotating and translating the wound cable at its proximal end can facilitate an exemplary helical imaging to take place over the entire extent of the balloon 328. During imaging, a control signal, derived from the reflection from the balloon surface (see FIGS. 4 and 5), can be used to generate an input to the focusing mechanism 325 to adaptively change the focal location. The wound cable 1212 and DCF 1211 can be attached to the housing 320 of the exemplary SECM arrangement/probe, which can contain a collimation lens 115, a grating 120, an objective lens 130, and the focusing mechanism 325. A 6.0 cm long, 2.5 cm diameter transparent centering balloon 328, can be affixed to the transparent sheath 1232. The distal end of the exemplary arrangement/probe can be terminated by a guide wire provision 1231.

Exemplary Probe Optics.

It is possible to reduce the size of the exemplary arrangement/probe further by developing customized optical and mechanical components. In order to minimize or reduce the rigid length, the collimation lens 115 can be fabricated to decrease the distance between the DCF 1211 and the lens 115. The grating 120 (e.g., Holographix, Hudson, Mass.) can be provided to have, e.g., maximum diffraction efficiency for the $2^{nd}$ order at 725 nm and for the $1^{st}$ order at about 1450 nm. The exemplary objective lens 130 (e.g., NA=0.4) can be provided (e.g., ZEMAX, Bellevue, Wash.) and produced (e.g., Optimax Systems Inc., Ontario) to have diffraction-limited performance throughout the optical sectioning depth range of about 100 μm in tissue. The objective lens 130 can be achromatic at 725 nm and 1450 nm, and can have a cylindrical surface to compensate for the astigmatism induced by the transparent catheter's sheath 1232.

Exemplary Wound Cable.

It is possible to utilize exemplary multi-layer wound drive shafts to scan distal optics within the patient for other imaging modalities. A custom wound cable 1212 can be fabricated (e.g., Asahi Intec, USA) and tested for the motion transduction accuracy and repeatability through the catheter.

Exemplary Balloon-Centering Catheter.

An exemplary balloon-centering catheter utilizing a transparent polycarbonate sheath 1232 (e.g., diameter=about 10 mm) and a transparent plastic balloon 328 (e.g., Advanced Polymers, Salem, N.H.; inflated diameter=about 25 mm) can be provided to house the probe optics and wound cable (e.g., Device company; Innovative Medical Design, Tyngsboro, Mass.). The exemplary catheter can be tested for transparency, flexibility, and trackability to ensure that it is suitable for intraesophageal imaging.

Exemplary Probe-Console Interface

An exemplary rotary junction (shown in an exemplary embodiment of the arrangement of FIG. 13) can be provided to couple light from the console to/from the probe and rotate the exemplary SECM arrangement/probe within the transparent sheath. In contrast to the exemplary OCT rotary junctions, the exemplary SECM optical rotary junction can transmit the imaging light from the light source 310 into the core 1351 of a double clad fiber ("DCF"). The inner cladding 1352 of the DCF can transmit laser marking light 1380, and can deliver imaging light returned from the sample to a spectrometer 1370.

Figure 13:
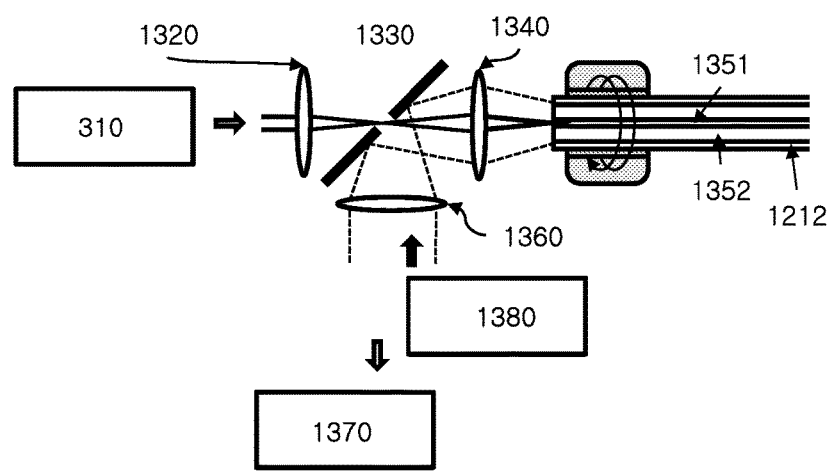
FIG. 13 is a schematic diagram of an exemplary rotary junction of the exemplary embodiment of a system according to the present disclosure.

To accomplish a separation of single- from multi-mode light, the exemplary rotary junction can contain two focusing lenses 1320, 1360 and a single-mode/multi-mode splitter, e.g., comprise a mirror 1330 with a central transparent aperture and a relay lens 1340 (see FIG. 13). The exemplary rotary junction can rotate the wound cable 1212 at 70 rpm.

In addition to coupling light from a static system to rotating catheter optics, the exemplary rotary junction can also transmit low electrical current to control the focusing mechanism. Further, the entire exemplary rotary junction can be affixed to a linearly scanning pullback stage, translating at a rate of about 0.1 mm/s, to enable helical scanning of the SECM probe optics. Motor encoder output from both rotational and linear motors can be digitized synchronously with the image signal to facilitate the exemplary SECM probe to return to any given image location in the patient for laser marking.

The exemplary optical rotary junction can be provided in Solid Works and simulated in ZEMAX. Exemplary design(s) can be optimized for maximum throughput and ease of manufacturing and tolerancing. The exemplary design(s) can be custom-machined, assembled and tested for single and double-passed throughput and rotational uniformity. The exemplary rotary junction can additionally be designed to fit within the standard motorized pull back trays.

Exemplary Console

Figure 14:
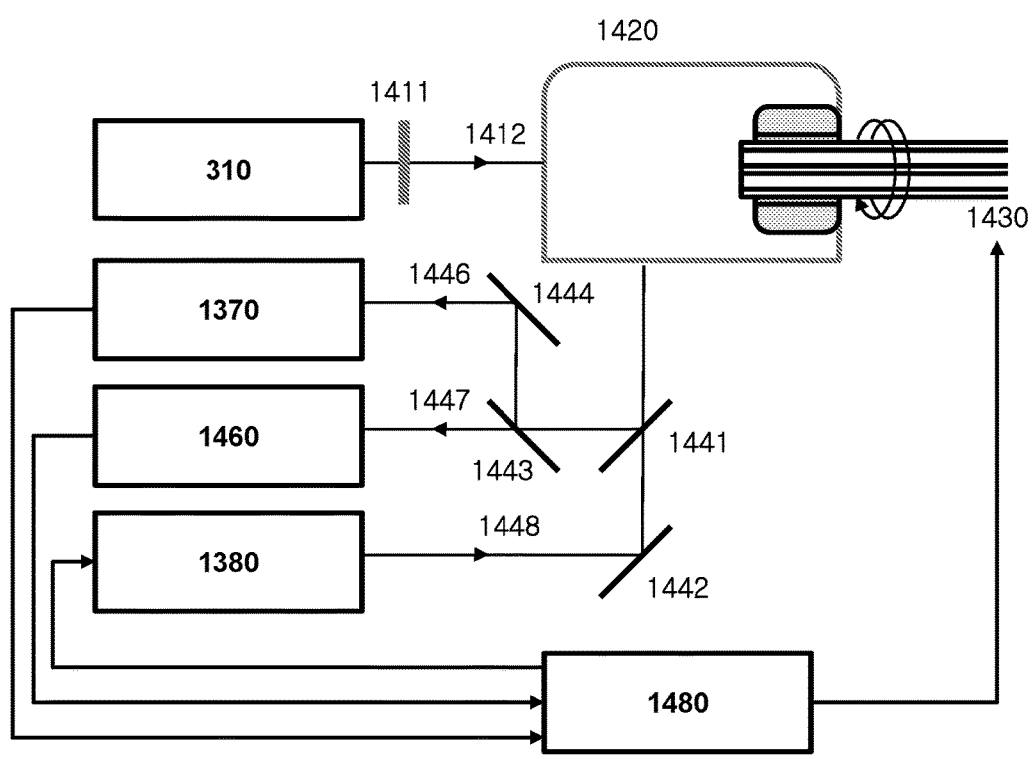
FIG. 14 is a schematic diagram of an exemplary SECM system of the exemplary embodiment according to the present disclosure.

An exemplary console (an example of a schematic diagram of which is shown in FIG. 14) can comprise the light sources and detectors used to image, mark, and can also be used to generate a feedback signal to control the focal location of the probe's objective lens. For imaging, light from a broadband light source 310 (e.g., Fianium SC450-6) can be filtered by a filter 1411 to have a broadband NIR spectrum 1421 of 725±30 nm. This exemplary wavelength range can be chosen so as to provide an appropriate compromise between resolution, penetration depth, and detector sensitivity. In addition, the center wavelength can be half that of the wavelength of the laser marking beam 1448 (e.g., about 1450 nm) from the high power laser 1380. By diffracting the imaging beam through the grating of the probe's second order and the marking laser through the first order, both can illuminate the same location on the sample.

Optical components, including the dichroic mirror 1441 and the mirror 1442 in the console, can route the single-mode imaging laser and multi-mode marking laser to the exemplary SECM probe 1430 through the rotary junction 1420. Remitted confocal light from the rotary junction 1420 can be divided by a dichroic mirror 1443 into two beams; the imaging beam 1446 that is directed to a spectrometer 1370 and the focusing beam 1447 that can be coupled to an optoelectronic apparatus 1460 for generating the auto-focusing feedback signal. The imaging beam 1446 and the focusing beam 1447 can cover different spectral regions. Each line in the image can be detected using a line-scan camera (e.g., SPL2048-140k, Basler) in the spectrometer 1380; exemplary digital image data can be transferred to the computer 1480 at a line rate of about 70 kHz and saved to a data recording system (e.g., Signatec DR-400) in real-time. The computer generates the control signal for the focusing mechanism in the SECM probe 1430.

Exemplary Adaptive Focusing Optoelectronics.

Figure 15:
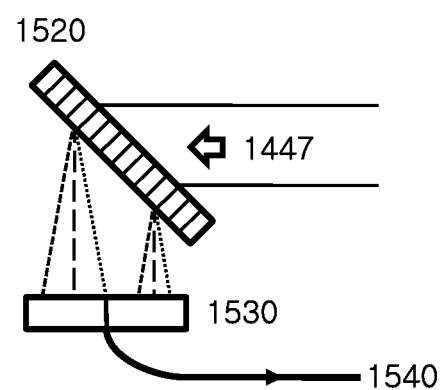
FIG. 15 is a schematic diagram of an exemplary embodiment of an optoelectronic apparatus for generating the auto-focusing feedback signal according to the present disclosure Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

An exemplary optoelectronic apparatus for generating the adaptive focus feedback signal according to the present disclosure can be provided (an exemplary diagram of which is shown in FIG. 15). As shown in FIG. 15, the focusing beam 1447 from the exemplary SECM probe (shown in FIG. 5) can be optically separated from the imaging beam 1446 (as shown in the diagram of FIG. 14), and a grating 1520 can be used to disperse its spectrum onto a position-sensitive detector 1530 (PSD; e.g., quadrant photodetector). The electrical signals from the individual cells in the PSD 1530 can be algebraically or mathematically processed (e.g., using a computing or processing arrangement) to provide the peak wavelength, which can correspond to the position of the inner surface of the balloon.

The balloon surface position can then be converted into a control signal that can drive the focusing mechanism and move the objective lens in the SECM probe. The output signal 1540 from the PSD 1530 can be fed to an analogue electric feedback circuit that controls the focusing mechanism directly or can be routed to the computer 1540 to be used for control purpose. By making this feedback/control independent of the imaging data acquisition, its response time can be much faster than that of the exemplary SECM arrangement/probe described herein above with reference to FIG. 3, resulting in an increase in imaging speed by more than a factor of, e.g., 4.

Exemplary Laser Marking for Guided Biopsy.

For example, two exemplary diode lasers (e.g., wavelength=about 1450 nm, power=about 200 mW each) can be polarization-multiplexed and integrated into the SECM system to create marks for guiding biopsy. Light from the diode lasers can be transmitted through a shutter and coupled into the inner cladding of the SECM probe through the rotary junction. A computer or other processing device(s) can control the intensities and exposure durations of the diode lasers. For safety reasons, e.g., the laser shutter can be configured to only allow a maximum of, e.g., about 10 seconds per exposure at any given site.

Exemplary System Integration.

Exemplary imaging and marking lasers can be tested for power and spatial coherence. Some or all optics can be tested for throughput and efficiency. The optical layout can be assembled on a small breadboard for incorporation into the cart. The imaging spectrometer can be fabricated and its spectral resolution and light throughput can be tested using standard techniques. Following assembly of the exemplary individual components, the exemplary system can be integrated into a portable, medical-grade cart. Software can be provided to control the rotary junction, the adaptive focusing mechanism, and the marking lasers using one or more computers. Existing software to facilitate the navigation of the image in a manner similar to that done with Google™ Earth, where pan and zoom quickly enable the viewer to focus on a precisely located area of interest, can be adapted for SECM datasets. Additional software user-interface inputs can be provided to allow the observer to quickly switch between different optical sections, delineate the target sites, and initiate laser marking.

Exemplary Specifications and Performance Expectations

Table 1 (below) depicts the exemplary specifications and objective performance targets (OPT) for the exemplary SECM arrangement/probe and system according to the present disclosure. The exemplary OPTs can be based on the preferences of comprehensive endoscopic confocal microscopy and prior experience with centering-balloon imaging of the esophagus. Meeting such exemplary OPTs can furthermore provide beneficial imaging performance. The exemplary arrangement/probe can have a deflated diameter of about 1.0 cm and a rigid length of about 4.5 cm—specifications that match that of commercially available, over-the-wire endoscopic ultrasound devices. Transverse and axial resolutions, governed by the number of modes transmitted through the inner cladding of the DCF can be better than critically sampled in the circumferential direction and Nyquist sampled along the longitudinal dimension. The longitudinal interval of about 72 μm between neighboring circumferential scans can provide optical sections at about 10 discrete depth locations and up to about 100 μm beyond the surface of the balloon. The exemplary marking beam can have a spot size of about 30 μm on the sample, which is sufficient for producing endoscopically visible marks on the esophageal surface in, e.g., about 2 seconds.

TABLE 1

| Specification | Value |
|---|---|
| Balloon diameter | 2.5 cm |
| Scan length | 5.0 cm |
| Sheath diameter | 1.0 cm |
| Rigid length | 4.5 cm |
| Center wavelength | 725 nm |
| Objective lens NA | 0.4 |
| Pixels/scan | 1024 |
| Line rate | 70 kHz |
| Rotation speed | 70 RPM |
| Pullback speed | 0.1 mm/s |
| Imaging duration | 10 min |
| OPT | |
| Single pass insertion loss | 5 dB |
| Transverse resolution | 1.6 μm |
| Axial resolution | 10 μm |
| Spectral FOV | 720 μm |
| Sectioning depth range | 100 μm |
| Dynamic focusing range | ±500 μm |
| Dynamic response of adaptive focusing | 2 Hz |
| Marking beam diameter | 30 μm |

The image-guided biopsy according to the exemplary embodiments of the present disclosure is expected to be safe and well-tolerable, detect previously unattainable subcellular and architectural information over large epithelial surfaces of the esophagus, and provide an effective method for endoscopic biopsy targeting. The long term impact of the exemplary embodiments of the present disclosure can also affect treatment as it can enable less invasive surgical techniques such as RF ablation, photodynamic therapy, or endoscopic mucosal resection to be used at an earlier stage of disease progression.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with imaging systems, and for example with those described in International Patent Publication WO 2005/047813 published May 26, 2005, U.S. Patent Publication No. 2006/0093276, published May 4, 2006, U.S. Patent Publication No. 2005/0018201, published Jan. 27, 2005 and U.S. Patent Publication No. 2002/0122246, published May 9, 2002, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for affecting a biological tissue, comprising:
   a radiation disperser arrangement which is configured to encode spatial information in an optical spectrum, and disperse first radiation and second radiation which have different spectral bands from one another;

at least one detector arrangement which is configured to receive and detect the first radiation; and at least one structural computer arrangement which is configured to:

receive first data associated with at least one image of at least one portion of the biological tissue obtained using an optical imaging technique, wherein the optical imaging technique includes a confocal microscopy technique that encodes spatial information in an optical spectrum, and wherein the first data is associated with the first radiation, based on the first data, forward the second radiation to the radiation disperser arrangement to cause a visible change that includes at least one endoscopically-visible marking on or in at least one location that is outside of and adjacent to the at least one portion, and cause a removal or a destruction of at least part of the at least one portion using image second data for the visible change on or in the at least one location.

2. The apparatus according to claim 1, wherein the at least one image for which the first data is received includes a volumetric image of the at least one portion.

3. The apparatus according to claim 2, wherein the volumetric image is a cylindrical image having a diameter of between about 10 mm to 100 mm.

4. The apparatus according to claim 2, wherein the volumetric image is a cylindrical image having an extension of at most about 1 m.

5. The apparatus according to claim 2, wherein the at least one structural computer arrangement is further configured to obtain data associated with the visible change, and guide a visualization to the at least one portion based on the data.

6. The apparatus according to claim 1, further comprising an ablation arrangement which is configured to ablate the at least one portion.

7. The apparatus according to claim 6, wherein the ablation of the at least one portion is performed by irradiating the at least one portion with the at least one electromagnetic radiation using the ablation arrangement.

8. The apparatus according to claim 1, wherein the at least one computer arrangement is situated in a probe, and further comprising an ablation arrangement provided in the probe which is controlled by the at least one computer arrangement to cause the visible change on or in the at least one portion.

9. The apparatus according to claim 8, wherein the at least one computer arrangement is configured to obtain the information via at least one wave-guiding arrangement, and the ablation arrangement provides the at least one electromagnetic radiation via the at least one wave-guiding arrangement to cause the visible change.

10. The apparatus according to claim 1, wherein the optical imaging technique includes an optical coherence tomography.

11. The apparatus according to claim 1, wherein the at least one computer arrangement is configured to cause a change to a superficial section of the at least one portion.

12. The apparatus according to claim 1, further comprising a biopsy arrangement which is configured to remove at least one section of the at least one portion that is substantially near or at a location of the visible change.

13. The apparatus according to claim 1, wherein the radiation disperser arrangement includes a grating.

14. A method for affecting a biological tissue, comprising:

encoding spatial information in an optical spectrum;

dispersing first radiation and second radiation which have different spectral bands from one another;

receiving and detecting the first radiation;

receiving first data associated with at least one image of at least one portion of the biological tissue obtained using an optical imaging technique, wherein the optical imaging technique includes a confocal microscopy technique that encodes spatial information in an optical spectrum, and wherein the first data is associated with the first radiation; and based on the first data, forwarding the second radiation to be dispersed so as to cause a visible change that includes at least one endoscopically-visible marking on or in at least one location that is outside of and adjacent to of the at least one portion; and using imaging second data for the visible change on or in the at least one location, causing a removal or a destruction of at least part of the at least one portion.

15. An apparatus for affecting a biological tissue, comprising:

a radiation disperser arrangement which is configured to encode spatial information in an optical spectrum, and disperse first radiation and second radiation which have different spectral bands from one another;

at least one detector arrangement which is configured to receive and detect the first radiation; and at least one computer arrangement which is configured to:

receive first data associated with at least one image of at least one portion of the biological tissue obtained using an optical imaging technique, wherein the optical imaging technique includes a confocal microscopy technique that encodes spatial information in an optical spectrum, and wherein the first data is associated with the first radiation, and based on the information, forward the second radiation to the dispersive arrangement to cause a visible change that includes at least one endoscopically-visible marking on or in at least one location that is outside of and adjacent to of the at least one portion.

16. The apparatus according to claim 15, wherein the radiation disperser arrangement includes a grating.

* * * * *